United States Patent [19]

Billiar et al.

[11] Patent Number: 5,468,630

[45] Date of Patent: Nov. 21, 1995

[54] CDNA CLONE FOR HUMAN INDUCIBLE NITRIC OXIDE SYNTHASE AND PROCESS FOR PREPARING SAME

[75] Inventors: Timothy R. Billiar; Andreas K. Nussler; David A. Geller; Richard L. Simmons, all of Pittsburgh, Pa.

[73] Assignee: University of Pittsburg of the Commonwealth System of Higher Education, Pittsburgh, Pa.

[21] Appl. No.: 314,917

[22] Filed: Sep. 28, 1994

Related U.S. Application Data

[63] Continuation of Ser. No. 981,344, Nov. 25, 1992, abandoned.

[51] Int. Cl.$^6$ .............................. C12N 9/02; C12N 15/53; C12N 15/70; C12N 15/79
[52] U.S. Cl. .................. 435/189; 435/69.1; 435/252.3; 435/252.33; 435/370.1; 536/23.2; 935/9; 935/14; 935/27; 935/68; 935/70; 935/73
[58] Field of Search .................... 435/69.1, 189, 435/252.3, 252.33, 320.1; 536/23.2

[56] References Cited

U.S. PATENT DOCUMENTS

| | | | |
|---|---|---|---|
| 4,652,639 | 3/1987 | Stabinsky | 536/23.1 |
| 4,882,282 | 11/1989 | Anderson et al. | 435/252.3 |
| 5,017,691 | 5/1991 | Lee et al. | 530/351 |
| 5,132,407 | 7/1992 | Stuehr et al. | 530/395 |
| 5,171,674 | 12/1992 | Stevens et al. | 435/69.1 |
| 5,189,957 | 2/1993 | Short et al. | 435/235.1 |
| 5,216,131 | 6/1993 | Lasky et al. | 530/350 |
| 5,223,425 | 6/1993 | Flier et al. | 435/240.2 |
| 5,236,844 | 8/1993 | Bassett et al. | 435/320.1 |
| 5,239,060 | 8/1993 | Kunkel et al. | 530/350 |
| 5,268,295 | 12/1993 | Serrero | 435/252.3 |
| 5,268,465 | 12/1993 | Bredt et al. | 435/252.3 |
| 5,278,299 | 1/1994 | Wong et al. | 536/53 |

OTHER PUBLICATIONS

Lowsenstein, et al.; 1992; Cloned and expressed macrophage nitric oxide synthase contrasts with the brain enzyme; Proc. Natl. Acad. Sci. USA; vol. 89, pp. 6711–6715.

Bredt, et al.; 1991; Cloned and expressed nitric oxide synthase structurally resembles cytochrome P–450 reductase; Nature; vol. 351; pp. 714–718.

Xie, et al.; 1992; Cloning and Characterization of Inducible Nitric oxide Synthase from Mouse Macrophages; Science; vol. 256; pp. 225–228.

Lyons, et al.; 1992; Molecular Cloning and Functional Expression of an Inducible Nitric Oxide Synthase from a Murine Macrophage Cell Line; The Journal of Biological Chemistry; vol. 267; pp. 6370–6374.

Marsden, et al.; 1992; Molecular cloning and characterization of human endothelial nitric oxide synthase; FEBS Letters; vol. 307, pp. 287–293.

Palmer, et al.; 1987; Nitric oxide release accounts for the biological activity of endothelium–derived relaxing factor; Nature; vol. 327, pp. 524–526.

Ignarro, et al.; 1987; Endothelium–derived relaxing factor produced and released from artery and vein is nitric oxide; Proc. Natl. Acad. Sci, USA; vol. 84, pp. 9265–9269.

Bredt and Snyder; 1989; Nitric oxide mediates glutamate–linked enhancement of cGMP levels in the cerebellum; Proc. Natl. Acad. Sci. USA; vol. 86, pp. 9030–9033.

(List continued on next page.)

*Primary Examiner*—Robert A. Wax
*Assistant Examiner*—William W. Moore
*Attorney, Agent, or Firm*—Eckert Seamans Cherin & Mellott

[57] ABSTRACT

A human tissue inducible nitric oxide synthase cDNA clone is disclosed. A process for preparing this cDNA clone coding for human tissue inducible nitric oxide synthase and for expressing the human tissue inducible nitric oxide synthase protein are provided.

23 Claims, 11 Drawing Sheets

OTHER PUBLICATIONS

Burnett, et al.; 1992; Nitric Oxide: A Physiologic Mediator of Penile Erection; Science; vol. 257; pp. 401–403.

Granger, et al.; 1988; Specific Amino Acid (L-Arginine) Requirement for the Microbiostatic Activity of Murine Macrophages; J. Clin. Invest.; vol. 81, pp. 1129–1136.

Hibbs, Jr., et al.; 1987; Macrophage Cytoxicity: Role for L-Arginine Deiminase and Imino Nitrogen Oxidation to Nitrite; Science; vol. 235, pp. 473–476.

Busse and Mulsch; 1990; Calcium-dependent nitric oxide synthesis in endothelial cytosol is mediated by calmodulin; FEBS Letters; vol. 265, pp. 133–136.

Kilbourn, et al.; 1990; $N^6$-Methyl-L-arginine inhibits tumor necrosis factor-induced hypotension: Implications for the involvement of nitric oxide; Proc. Natl. Acad. Sci. USA; vol. 87, pp. 3629–3632.

Mulligan, et al.; 1992; Lung Injury after deposition of IgA immune complexes; J. Immunology vol. 148, pp. 3086–3092.

Corbett, et al.; 1991; Interleukin-1β-induced Formation of EPR-detectable Iron-Nitrosyl Complexes in Islets of Langerhans; The Journal of Biological Chemistry; vol. 266, pp. 21351–21354.

Nussler, et al.; 1992; FASEB Meeting; Anaheim, Calif. Stimulation of Nitric Oxide in Human Hepatocytes By Cytokines, Abst. 5200.

Nussler, et al.; 1992; Stimulation of the Nitric Oxide Synthase pathway in Human Hepatocytes by Cytokines and Endotoxin; J. Exp. med. vol. 176, pp. 261–264.

J. C. Drapier; 1991; Res. Immoc., 39th Forum In Immunoc.; See specifically pp. 557, 562 and 589–590.

Summers and Smith; 1988; A Manual of Methods for Baculovirus Vectors and Insect Cell Culture Procedures; Texas Agricultural Experiment Station Bulletin No. 1555, pp. 3–56.

Evans, et al.; 1992; Purification of a distinctive form of endotoxin-induced nitric oxide synthase from rat liver; Proc. Natl. Acad. Sci. USA; vol. 89, pp. 5361–5365.

Curran, et al.; 1991; Nitric oxide and nitric oxide-generating compounds inhibit hepatocyte protein synthesis; FASEB; vol. 5, pp. 2085–2092.

Billiar, et al.; 1992; Association between synthesis and release of cGMP and nitric oxide biosynthesis by hepatocytes; American Physiological Society; pp. C1077–C1082.

Billiar, et al.; 1990; Inducible Cytosolic Enzyme Activity for the Production of Nitrogen oxides from L-arginine in Hepatoycytes; Bioch. Biophys. Res. Comm; vol. 168, pp. 1034–1040.

Billiar, et al.; 1989; An L-arginine-dependent Mechanism Mediates Kupffer Cell Inhibition of Hepatocyte Protein Synthesis in Vitro; J. Exp. Med.; vol. 169; pp. 1467–1472.

Stadler, et al.; 1991; Effect of exogenous and endogenous nitric oxide on mitochondrial American Physiological Society; pp. C910–C916.

Ochoa, et al.; 1991; Nitrogen Oxide Levels in Patients after Trauma and During Sepsis, Ann. Surg. 214: 621–626.

Billiar, et al.; 1990; Modulation of Nitrogen Oxide Synthesis In Vivo J. Leuk. Biol. 48: pp. 565–569.

Ochoa, et al.; 1992; Increased Circulating Nitrogen Oxides After Human Tumor Immunotherapy: Correlation with Toxic Hemodynamic Changes; Journal of the National Cancer Institute; pp. 864–867.

Curran, et al.; 1990; Multiple Cytokines Are Required to Induce Hepatocyte Nitric Oxide Production and Inhibit Total Protein Synthesis; Ann. Surg. 212: pp. 462–471.

Curran, et al.; 1989; Hepatocytes Produce Nitrogen Oxides from L-Arginine in Response to Inflammatory Products of Kupffer Cells; J. Exp. Med.; vol. 170, pp. 1769–1774.

Finkel, et al.; 1912, Negative Inotropic Effects of Cytokines on the Heart Mediated by Nitric Oxide Science 257: 387'389.

Billiar, T. R., et al., 1991, Research in Immunology, 142:584–586.

Hibbs, J. B., Jr., et al., 1992, Journal & Clinical Investigation 89:867–877.

Denis, M., 1991, Journal of Leukocyte Biology, 49:380–387.

Hunt, M. C. A., et al., 1992, Journal of Heptology, 14:146–150.

Munñoz-Fernández, M. A., et al., 1992, Immunology Letters, 33:35–40.

Cameron, M. L., et al., 1990, American Review of Respiratory Disease, 142:1313–1319.

Sherman, M. P., et al., 1991, Journal of Photozoology, 38(6):2345–2365.

James, S. L., et al., 1990, Journal of Immunology, 145:2686–2690.

Padgett, E. L., et al., 1992, Biochemical and Biophysical Research Communications, 186(2):775–781.

Denis, M., 1994, Journal of Leukocyte Biology 55:682–684.

Bredt, D. S., et al., 1990, Proceedings of the National Academy of Sciences, U.S.A. 87:682–685.

Billiar, T. R., et al., 1991, FASEB Journal 5(5): A1344, Abstract No. 5642.

Knowles, R. G., et al., 1990, Biochemical and Biophysical Research Communications, 172(3): 1042–1048.

Stadler, J., et al., 1991, Archives of Surgery, 126(2):186–191.

Nathan, C., 1991, Research in Immunology, 142(7):600–602.

Wright, C. E., 1992, Cardiovascular Research, 26(1): 48–57.

DiSilvio, M., et al., 1992 Gastroenterology 102: A801, abstract.

Klatt, P., et al., 1992, Journal of Biological Chemistry, 267(16):11374–11378.

Oguchi, S., et al., 1992, FEBS Letters, 308(1):22–25.

Harbrecht, B. G., et al., 1992, Journal of Leukocyte Biology, 52(4):390–394.

Harbrecht, B. G., et al., 1992, Critical Care Medicine 20:1568–1574.

Nussler, A. K., et al., 1992, Journal of Leukocyte Biology, Supplement 3:137, Abstract No. 146.

Kontkamp, E., et al., 1986, DNA, 5(6):511–517

Sherman, P. A., et al., 1993, Biochemistry, 32:11600–11605.

Chartrain, N. A., et al., 1994, Proceedings of the National Academy of Sciences, U.S.A., 269(9):6765–6772.

Hokari, A., et al., 1994, Journal of Biochemistry 116:575–581.

Charles, I. G., et al., 1993, Proceedings of the National Academy of Sciences, U.S.A., 90: 11419–11423.

Lamas, S., et al., 1992, Proceedings of the National Academy of Sciences, U.S.A., 89(14):6348–6352.

Lelchuk, R., et al., 1992, The Journal of Pharmacology and Experimental Therapeutics, 262(3):1220–1224.

Janssens, S. P., et al., 1992, The Journal of Biological Chemistry, 267(21):14519–14522.

Siebert, P. D., et al., 1992, Nature, 359(6395):557–558.

Knowles, R. G., et al., 1990, The Biochemical Journal, 270:833–836.

Salter, M., et al., 1991, FEBS Letters, 291(1):145–149.

Springall, D. R., et al., FEBS Letters, 29(1):145–149.

Springall, D. R., et al., 1992, Histochemistry, 98(4):259–266.

Pfeilschifter, J., et al., 1992, European Journal of Biochemistry, 203 (1–2):251–255.

Vanhoutte, P. M., 1992, The Japanese Journal of Pharmacology, *International Symposium on Smooth Muscle:* 192P–199P.

Nakayama, D. K., et al., 1992, American Journal of Respiratory Cell Molecular Biology, 7:471–476.

Dawson, T. M., et al., 1991, Proceedings of the National Academy of Sciences, U.S.A., 88(17):7797–7801.

Yui, Y., et al., 1991, The Journal of Biological Chemistry, 266(19):12544–12547.

Hevel, J. M., et al., 1991, The Journal of Biological Chemistry, 266(34):22789–22791.

Oshima, H., et al., 1992, Biochemical and Biophysical Research Communications, 183(1):238–244.

```
CTGCTTTAAA ATCTCTCGGC CACCTTTGAT GAGGGGACTG GGCAGTTCTA GACAGTCCCG        60

AAGTTCTCAA GGCACAGGTC TCTTCCTGGT TTGACTGTCC TTACCCCGGG GAGGCAGTGC       120

AGCCAGCTGC AAGCCCCACA GTGAAGAACA TCTGAGCTCA AATCCAGATA AGTGACATAA       180

GTGACCTGCT TTGTAAAGCC ATAGAG ATG GCC TGT CCT TGG AAA TTT CTG TTC       233
                              Met Ala Cys Pro Trp Lys Phe Leu Phe
                               1                    5
```

|  |  |  |  |  |  |  |  |  |  |  |  |  |  |  |  |
|---|---|---|---|---|---|---|---|---|---|---|---|---|---|---|---|
| AAG | ACC | AAA | TTC | CAC | CAG | TAT | GCA | ATG | AAT | GGG | GAA | AAA | GAC | ATC | AAC |
| Lys | Thr | Lys | Phe | His | Gln | Tyr | Ala | Met | Asn | Gly | Glu | Lys | Asp | Ile | Asn |
|  | 10 |  |  |  | 15 |  |  |  |  | 20 |  |  |  |  | 25 |

281

```
AAC AAT GTG GAG AAA GCC CCC TGT GCC ACC TCC AGT CCA GTG ACA CAG       329
Asn Asn Val Glu Lys Ala Pro Cys Ala Thr Ser Ser Pro Val Thr Gln
             30              35                      40

GAT GAC CTT CAG TAT CAC AAC CTC AGC AAG CAG CAG AAT GAG TCC CCG       377
Asp Asp Leu Gln Tyr His Asn Leu Ser Lys Gln Gln Asn Glu Ser Pro
             45              50                      55

CAG CCC CTC GTG GAG ACG GGA AAG AAG TCT CCA GAA TCT CTG GTC AAG       425
Gln Pro Leu Val Glu Thr Gly Lys Lys Ser Pro Glu Ser Leu Val Lys
             60              65                      70

CTG GAT GCA ACC CCA TTG TCC TCC CCA CGG CAT GTG AGG ATC AAA AAC       473
Leu Asp Ala Thr Pro Leu Ser Ser Pro Arg His Val Arg Ile Lys Asn
     75                  80                  85

TGG GGC AGC GGG ATG ACT TTC CAA GAC ACA CTT CAC CAT AAG GCC AAA       521
Trp Gly Ser Gly Met Thr Phe Gln Asp Thr Leu His His Lys Ala Lys
 90              95                  100                 105

GGG ATT TTA ACT TGC AGG TCC AAA TCT TGC CTG GGG TCC ATT ATG ACT       569
Gly Ile Leu Thr Cys Arg Ser Lys Ser Cys Leu Gly Ser Ile Met Thr
                 110                 115                 120

CCC AAA AGT TTG ACC AGA GGA CCC AGG GAC AAG CCT ACC CCT CCA GAT       617
Pro Lys Ser Leu Thr Arg Gly Pro Arg Asp Lys Pro Thr Pro Pro Asp
             125                 130                 135
```

Fig. 1a.

```
GAG CTT CTA CCT CAA GCT ATC GAA TTT GTC AAC CAA TAT TAC GGC TCC        665
Glu Leu Leu Pro Gln Ala Ile Glu Phe Val Asn Gln Tyr Tyr Gly Ser
        140             145                 150

TTC AAA GAG GCA AAA ATA GAG GAA CAT CTG GCC AGG GTG GAA GCG GTA        713
Phe Lys Glu Ala Lys Ile Glu Glu His Leu Ala Arg Val Glu Ala Val
    155             160                 165

ACA AAG GAG ATA GAA ACA ACA GGA ACC TAC CAA CTG ACG GGA GAT GAG        761
Thr Lys Glu Ile Glu Thr Thr Gly Thr Tyr Gln Leu Thr Gly Asp Glu
170             175                 180                 185

CTC ATC TTC GCC ACC AAG CAG GCC TGG CGC AAT GCC CCA CGC TGC ATT        809
Leu Ile Phe Ala Thr Lys Gln Ala Trp Arg Asn Ala Pro Arg Cys Ile
                190                 195                 200

GGG AGG ATC CAG TGG TCC AAC CTG CAG GTC TTC GAT GCC CGC AGC TGT        857
Gly Arg Ile Gln Trp Ser Asn Leu Gln Val Phe Asp Ala Arg Ser Cys
            205                 210                 215

TCC ACT GCC CGG GAA ATG TTT GAA CAC ATC TGC AGA CAC GTG CGT TAC        905
Ser Thr Ala Arg Glu Met Phe Glu His Ile Cys Arg His Val Arg Tyr
        220                 225                 230

TCC ACC AAC AAT GGC AAC ATC AGG TCG GCC ATC ACC GTG TTC CCC CAG        953
Ser Thr Asn Asn Gly Asn Ile Arg Ser Ala Ile Thr Val Phe Pro Gln
    235                 240                 245

CGG AGT GAT GGC AAG CAC GAC TTC CGG GTG TGG AAT GCT CAG CTC ATC       1001
Arg Ser Asp Gly Lys His Asp Phe Arg Val Trp Asn Ala Gln Leu Ile
250                 255                 260                 265

CGC TAT GCT GGC TAC CAG ATG CCA GAT GGC AGC ATC AGA GGG GAC CCT       1049
Arg Tyr Ala Gly Tyr Gln Met Pro Asp Gly Ser Ile Arg Gly Asp Pro
                270                 275                 280

GCC AAC GTG GAA TTC ACT CAG CTG TGC ATC GAC CTG GGC TGG AAG CCC       1097
Ala Asn Val Glu Phe Thr Gln Leu Cys Ile Asp Leu Gly Trp Lys Pro
            285                 290                 295

AAG TAC GGC CGC TTC GAT GTG GTC CCC CTG GTC CTG CAG GCC AAT GGC       1145
Lys Tyr Gly Arg Phe Asp Val Val Pro Leu Val Leu Gln Ala Asn Gly
        300                 305                 310
```

*Fig. 1b.*

```
CGT GAC CCT GAG CTC TTC GAA ATC CCA CCT GAC CTT GTG CTT GAG GTG    1193
Arg Asp Pro Glu Leu Phe Glu Ile Pro Pro Asp Leu Val Leu Glu Val
    315                 320                 325

GCC ATG GAA CAT CCC AAA TAC GAG TGG TTT CGG GAA CTG GAG CTA AAG    1241
Ala Met Glu His Pro Lys Tyr Glu Trp Phe Arg Glu Leu Glu Leu Lys
330                 335                 340                 345

TGG TAC GCC CTG CCT GCA GTG GCC AAC ATG CTG CTT GAG GTG GGC GGC    1289
Trp Tyr Ala Leu Pro Ala Val Ala Asn Met Leu Leu Glu Val Gly Gly
                350                 355                 360

CTG GAG TTC CCA GGG TGC CCC TTC AAT GGC TGG TAC ATG GGC ACA GAG    1337
Leu Glu Phe Pro Gly Cys Pro Phe Asn Gly Trp Tyr Met Gly Thr Glu
            365                 370                 375

ATC GGA GTC CGG GAC TTC TGT GAC GTC CAG CGC TAC AAC ATC CTG GAG    1385
Ile Gly Val Arg Asp Phe Cys Asp Val Gln Arg Tyr Asn Ile Leu Glu
        380                 385                 390

GAA GTG GGC AGG AGA ATG GGC CTG GAA ACG CAC AAG CTG GCC TCG CTC    1433
Glu Val Gly Arg Arg Met Gly Leu Glu Thr His Lys Leu Ala Ser Leu
    395                 400                 405

TGG AAA GAC CAG GCT GTC GTT GAG ATC AAC ATT GCT GTG ATC CAT AGT    1481
Trp Lys Asp Gln Ala Val Val Glu Ile Asn Ile Ala Val Ile His Ser
410                 415                 420                 425

TTT CAG AAG CAG AAT GTG ACC ATC ATG GAC CAC CAC TCG GCT GCA GAA    1529
Phe Gln Lys Gln Asn Val Thr Ile Met Asp His His Ser Ala Ala Glu
                430                 435                 440

TCC TTC ATG AAG TAC ATG CAG AAT GAA TAC CGG TCC CGT GGG GGC TGC    1577
Ser Phe Met Lys Tyr Met Gln Asn Glu Tyr Arg Ser Arg Gly Gly Cys
            445                 450                 455

CCG GCA GAC TGG ATT TGG CTG GTC CCT CCC ATG TCT GGG AGC ATC ACC    1625
Pro Ala Asp Trp Ile Trp Leu Val Pro Pro Met Ser Gly Ser Ile Thr
        460                 465                 470

CCC GTG TTT CAC CAG GAG ATG CTG AAC TAC GTC CTG TCC CCT TTC TAC    1673
Pro Val Phe His Gln Glu Met Leu Asn Tyr Val Leu Ser Pro Phe Tyr
    475                 480                 485
```

*Fig. 1C.*

```
TAC TAT CAG GTA GAG GCC TGG AAA ACC CAT GTC TGG CAG GAC GAG AAG    1721
Tyr Tyr Gln Val Glu Ala Trp Lys Thr His Val Trp Gln Asp Glu Lys
490             495             500             505

CGG AGA CCC AAG AGA AGA GAG ATT CCA TTG AAA GTC TTG GTC AAA GCT    1769
Arg Arg Pro Lys Arg Arg Glu Ile Pro Leu Lys Val Leu Val Lys Ala
                510             515             520

GTG CTC TTT GCC TGT ATG CTG ATG CGC AAG ACA ATG GCG TCC CGA GTC    1817
Val Leu Phe Ala Cys Met Leu Met Arg Lys Thr Met Ala Ser Arg Val
            525             530             535

AGA GTC ACC ATC CTC TTT GCG ACA GAG ACA GGA AAA TCA GAG GCG CTG    1865
Arg Val Thr Ile Leu Phe Ala Thr Glu Thr Gly Lys Ser Glu Ala Leu
        540             545             550

GCC TGG GAC CTG GGG GCC TTA TTC AGC TGT GCC TTC AAC CCC AAG GTT    1913
Ala Trp Asp Leu Gly Ala Leu Phe Ser Cys Ala Phe Asn Pro Lys Val
        555             560             565

GTC TGC ATG GAT AAG TAC AGG CTG AGC TGC CTG GAG GAG GAA CGG CTG    1961
Val Cys Met Asp Lys Tyr Arg Leu Ser Cys Leu Glu Glu Glu Arg Leu
570             575             580             585

CTG TTG GTG GTG ACC AGT ACG TTT GGC AAT GGA GAC TGC CCT GGC AAT    2009
Leu Leu Val Val Thr Ser Thr Phe Gly Asn Gly Asp Cys Pro Gly Asn
            590             595             600

GGA GAG AAA CTG AAG AAA TCG CTC TTC ATG CTG AAA GAG CTC AAC AAC    2057
Gly Glu Lys Leu Lys Lys Ser Leu Phe Met Leu Lys Glu Leu Asn Asn
            605             610             615

AAA TTC AGG TAC GCT GTG TTT GGC CTC GGC TCC AGC ATG TAC CCT CGG    2105
Lys Phe Arg Tyr Ala Val Phe Gly Leu Gly Ser Ser Met Tyr Pro Arg
        620             625             630

TTC TGC GCC TTT GCT CAT GAC ATT GAT CAG AAG CTG TCC CAC CTG GGG    2153
Phe Cys Ala Phe Ala His Asp Ile Asp Gln Lys Leu Ser His Leu Gly
        635             640             645

GCC TCT CAG CTC ACC CCG ATG GGA GAA GGG GAT GAG CTC AGT GGG CAG    2201
Ala Ser Gln Leu Thr Pro Met Gly Glu Gly Asp Glu Leu Ser Gly Gln
650             655             660             665

GAG GAC GCC TTC CGC AGC TGG GCC GTG CAA ACC TTC AAG GCA GCC TGT    2249
Glu Asp Ala Phe Arg Ser Trp Ala Val Gln Thr Phe Lys Ala Ala Cys
                670             675             680
```

Fig. 1d.

```
GAG ACG TTT GAT GTC CGA GGC AAA CAG CAC ATT CAG ATC CCC AAG CTC    2297
Glu Thr Phe Asp Val Arg Gly Lys Gln His Ile Gln Ile Pro Lys Leu
            685                 690                 695

TAC ACC TCC AAT GTG ACC TGG GAC CCG CAC CAC TAC AGG CTC GTG CAG    2345
Tyr Thr Ser Asn Val Thr Trp Asp Pro His His Tyr Arg Leu Val Gln
            700                 705                 710

GAC TCA CAG CCT TTG GAC CTC AGC AAA GCC CTC AGC AGC ATG CAT GCC    2393
Asp Ser Gln Pro Leu Asp Leu Ser Lys Ala Leu Ser Ser Met His Ala
            715                 720                 725

AAG AAC GTG TTC ACC ATG AGG CTC AAA TCT CGG CAG AAT CTA CAA AGT    2441
Lys Asn Val Phe Thr Met Arg Leu Lys Ser Arg Gln Asn Leu Gln Ser
730                 735                 740                 745

CCG ACA TCC AGC CGT GCC ACC ATC CTG GTG GAA CTC TCC TGT GAG GAT    2489
Pro Thr Ser Ser Arg Ala Thr Ile Leu Val Glu Leu Ser Cys Glu Asp
            750                 755                 760

GGC CAA GGC CTG AAC TAC CTG CCG GGG GAG CAC CTT GGG GTT TGC CCA    2537
Gly Gln Gly Leu Asn Tyr Leu Pro Gly Glu His Leu Gly Val Cys Pro
            765                 770                 775

GGC AAC CAG CCG GCC CTG GTC CAA GGC ATC CTG GAG CGA GTG GTG GAT    2585
Gly Asn Gln Pro Ala Leu Val Gln Gly Ile Leu Glu Arg Val Val Asp
            780                 785                 790

GGC CCC ACA CCC CAC CAG ACA GTG CGC CTG GAG GAC CTG GAT GAG AGT    2633
Gly Pro Thr Pro His Gln Thr Val Arg Leu Glu Asp Leu Asp Glu Ser
            795                 800                 805

GGC AGC TAC TGG GTC AGT GAC AAG AGG CTG CCC CCC TGC TCA CTC AGC    2681
Gly Ser Tyr Trp Val Ser Asp Lys Arg Leu Pro Pro Cys Ser Leu Ser
810                 815                 820                 825

CAG GCC CTC ACC TAC TCC CCG GAC ATC ACC ACA CCC CCA ACC CAG CTG    2729
Gln Ala Leu Thr Tyr Ser Pro Asp Ile Thr Thr Pro Pro Thr Gln Leu
            830                 835                 840

CTG CTC CAA AAG CTG GCC CAG GTG GCC ACA GAA GAG CCT GAG AGA CAG    2777
Leu Leu Gln Lys Leu Ala Gln Val Ala Thr Glu Glu Pro Glu Arg Gln
            845                 850                 855
```

Fig. 1e.

```
AGG CTG GAG GCC CTG TGC CAG CCC TCA GAG TAC AGC AAG TGG AAG TTC        2825
Arg Leu Glu Ala Leu Cys Gln Pro Ser Glu Tyr Ser Lys Trp Lys Phe
        860             865             870

ACC AAC AGC CCC ACA TTC CTG GAG GTG CTA GAG GAG TTC CCG TCC CTG        2873
Thr Asn Ser Pro Thr Phe Leu Glu Val Leu Glu Glu Phe Pro Ser Leu
    875             880             885

CGG GTG TCT GCT GGC TTC CTG CTT TCC CAG CTC CCC ATT CTG AAG CCC        2921
Arg Val Ser Ala Gly Phe Leu Leu Ser Gln Leu Pro Ile Leu Lys Pro
890             895             900                         905

AGG TTC TAC TCC ATC AGC TCC TCC CGG GAT CAC ACG CCC ACG GAG ATC        2969
Arg Phe Tyr Ser Ile Ser Ser Ser Arg Asp His Thr Pro Thr Glu Ile
                910             915             920

CAC CTG ACT GTG GCC GTG GTC ACC TAC CAC ACC GGA GAT GGC CAG GGT        3017
His Leu Thr Val Ala Val Val Thr Tyr His Thr Gly Asp Gly Gln Gly
            925             930             935

CCC CTG CAC CAC GGT GTC TGC AGC ACA TGG CTC AAC AGC CTG AAG CCC        3065
Pro Leu His His Gly Val Cys Ser Thr Trp Leu Asn Ser Leu Lys Pro
        940             945             950

CAA GAC CCA GTG CCC TGC TTT GTG CGG AAT GCC AGC GCC TTC CAC CTC        3113
Gln Asp Pro Val Pro Cys Phe Val Arg Asn Ala Ser Ala Phe His Leu
    955             960             965

CCC GAG GAT CCC TCC CAT CCT TGC ATC CTC ATC GGG CCT GGC ACA GGC        3161
Pro Glu Asp Pro Ser His Pro Cys Ile Leu Ile Gly Pro Gly Thr Gly
970             975             980                         985

ATC GTG CCC TTC CGC AGT TTC TGG CAG CAA CGG CTC CAT GAC TCC CAG        3209
Ile Val Pro Phe Arg Ser Phe Trp Gln Gln Arg Leu His Asp Ser Gln
                990             995             1000

CAC AAG GGA GTG CGG GGA GGC CGC ATG ACC TTG GTG TTT GGG TGC CGC        3257
His Lys Gly Val Arg Gly Gly Arg Met Thr Leu Val Phe Gly Cys Arg
            1005            1010            1015

CGC CCA GAT GAG GAC CAC ATC TAC CAG GAG GAG ATG CTG GAG ATG GCC        3305
Arg Pro Asp Glu Asp His Ile Tyr Gln Glu Glu Met Leu Glu Met Ala
        1020            1025            1030

CAG AAG GGG GTG CTG CAT GCG GTG CAC ACA GCC TAT TCC CGC CTG CCT        3353
Gln Lys Gly Val Leu His Ala Val His Thr Ala Tyr Ser Arg Leu Pro
    1035            1040            1045
```

Fig. 1f.

```
GGC AAG CCC AAG GTC TAT GTT CAG GAC ATC CTG CGG CAG CAG CTG GCC    3401
Gly Lys Pro Lys Val Tyr Val Gln Asp Ile Leu Arg Gln Gln Leu Ala
1050            1055            1060            1065

AGC GAG GTG CTC CGT GTG CTC CAC AAG GAG CCA GGC CAC CTC TAT GTT    3449
Ser Glu Val Leu Arg Val Leu His Lys Glu Pro Gly His Leu Tyr Val
        1070            1075            1080

TGC GGG GAT GTG CGC ATG GCC CGG GAC GTG GCC CAC ACC CTG AAG CAG    3497
Cys Gly Asp Val Arg Met Ala Arg Asp Val Ala His Thr Leu Lys Gln
            1085            1090            1095

CTG GTG GCT GCC AAG CTG AAA TTG AAT GAG GAG CAG GTC GAG GAC TAT    3545
Leu Val Ala Ala Lys Leu Lys Leu Asn Glu Glu Gln Val Glu Asp Tyr
        1100            1105            1110

TTC TTT CAG CTC AAG AGC CAG AAG CGC TAT CAC GAA GAT ATC TTC GGT    3593
Phe Phe Gln Leu Lys Ser Gln Lys Arg Tyr His Glu Asp Ile Phe Gly
        1115            1120            1125

GCT GTA TTT CCT TAC GAG GCG AAG AAG GAC AGG GTG GCG GTG CAG CCC    3641
Ala Val Phe Pro Tyr Glu Ala Lys Lys Asp Arg Val Ala Val Gln Pro
1130            1135            1140            1145

AGC AGC CTG GAG ATG TCA GCG CTC TGAGGGCCTA CAGGAGGGGT TAAAGCTGCC   3695
Ser Ser Leu Glu Met Ser Ala Leu
                1150

GGCACAGAAC TTAAGGATGG AGCCAGCTCT GCATTATCTG AGGTCACAGG GCCTGGGGAG  3755

ATGGAGGAAA GTGATATCCC CCAGCCTCAA GTCTTATTTC CTCAACGTTG CTCCCCATCA  3815

AGCCCTTTAC TTGACCTCCT AACAAGTAGC ACCCTGGATT GATCGGAGCC TCCTCTCTCA  3875

AACTGGGGCC TCCCTGGTCC CTTGGAGACA AAATCTTAAA TGCCAGGCCT GGCGAGTGGG  3935

TGAAAGATGG AACTTGCTGC TGAGTGCACC ACTTCAAGTG ACCACCAGGA GGTGCTATCG  3995

CACCACTGTG TATTTAACTG CCTTGTGTAC AGTTATTTAT GCCTCTGTAT TTAAAAAACT  4055

AACACCCAGT CTGTTCCCCA TGGCCACTTG GGTCTTCCCT GTATGATTCC TTGATGGAGA  4115

TATTTACATG AATTGCATTT TACTTTAATC                                  4145
```

Fig. 1g.

NB 25 Mac NOS insert
18° exposure
2/28/92

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4145 base pairs
        ( B ) TYPE: nucleic acid
        ( C ) STRANDEDNESS: double
        ( D ) TOPOLOGY: linear ( i i ) MOLECULE TYPE: cDNA
        ( A ) DESCRIPTION: Human Hepatocyte Inducible Nitric Oxide
            Synthase cDNA Clone ( i i i ) HYPOTHETICAL: NO ( i v ) ANTI-SENSE: NO ( v i ) ORIGINAL SOURCE:
        ( F ) TISSUE TYPE: Induced Human Hepatocyte RNA ( v i i ) IMMEDIATE SOURCE:
        ( A ) LIBRARY: Lambda Zap II cDNA
        ( B ) CLONE: pHINOS ( v i i i ) POSITION IN GENOME:
        ( A ) CHROMOSOME/SEGMENT: unknown
        ( B ) MAP POSITION: unknown
        ( C ) UNITS: unknown ( i x ) FEATURE:
        ( A ) NAME/KEY: CDS
        ( B ) LOCATION: 207..3668
        ( C ) IDENTIFICATION METHOD: Experiment ( x i ) SEQUENCE DESCRIPTION: SEQ ID NO:1:

```
CTGCTTTAAA   ATCTCTCGGC   CACCTTTGAT   GAGGGGACTG   GGCAGTTCTA   GACAGTCCCG                            60

AAGTTCTCAA   GGCACAGGTC   TCTTCCTGGT   TTGACTGTCC   TTACCCCGGG   GAGGCAGTGC                           120

AGCCAGCTGC   AAGCCCCACA   GTGAAGAACA   TCTGAGCTCA   AATCCAGATA   AGTGACATAA                           180

GTGACCTGCT   TTGTAAAGCC   ATAGAG ATG   GCC   TGT   CCT   TGG   AAA   TTT   CTG   TTC                 233
                                  Met   Ala   Cys   Pro   Trp   Lys   Phe   Leu   Phe
                                   1                       5

AAG   ACC   AAA   TTC   CAC   CAG   TAT   GCA   ATG   AAT   GGG   GAA   AAA   GAC   ATC   AAC         281
Lys   Thr   Lys   Phe   His   Gln   Tyr   Ala   Met   Asn   Gly   Glu   Lys   Asp   Ile   Asn
 10                15                           20                            25

AAC   AAT   GTG   GAG   AAA   GCC   CCC   TGT   GCC   ACC   TCC   AGT   CCA   GTG   ACA   CAG         329
```

-continued

| | | | | | | | | | | | | | | | | |
|---|---|---|---|---|---|---|---|---|---|---|---|---|---|---|---|---|
| Asn | Asn | Val | Glu | Lys<br>30 | Ala | Pro | Cys | Ala | Thr<br>35 | Ser | Ser | Pro | Val | Thr<br>40 | Gln | |
| GAT | GAC | CTT | CAG | TAT | CAC | AAC | CTC | AGC | AAG | CAG | CAG | AAT | GAG | TCC | CCG | 377 |
| Asp | Asp | Leu | Gln<br>45 | Tyr | His | Asn | Leu | Ser<br>50 | Lys | Gln | Gln | Asn | Glu<br>55 | Ser | Pro | |
| CAG | CCC | CTC | GTG | GAG | ACG | GGA | AAG | AAG | TCT | CCA | GAA | TCT | CTG | GTC | AAG | 425 |
| Gln | Pro | Leu<br>60 | Val | Glu | Thr | Gly | Lys<br>65 | Lys | Ser | Pro | Glu | Ser<br>70 | Leu | Val | Lys | |
| CTG | GAT | GCA | ACC | CCA | TTG | TCC | TCC | CCA | CGG | CAT | GTG | AGG | ATC | AAA | AAC | 473 |
| Leu | Asp<br>75 | Ala | Thr | Pro | Leu | Ser<br>80 | Ser | Pro | Arg | His | Val<br>85 | Arg | Ile | Lys | Asn | |
| TGG | GGC | AGC | GGG | ATG | ACT | TTC | CAA | GAC | ACA | CTT | CAC | CAT | AAG | GCC | AAA | 521 |
| Trp<br>90 | Gly | Ser | Gly | Met | Thr<br>95 | Phe | Gln | Asp | Thr | Leu<br>100 | His | His | Lys | Ala | Lys<br>105 | |
| GGG | ATT | TTA | ACT | TGC | AGG | TCC | AAA | TCT | TGC | CTG | GGG | TCC | ATT | ATG | ACT | 569 |
| Gly | Ile | Leu | Thr | Cys<br>110 | Arg | Ser | Lys | Ser | Cys<br>115 | Leu | Gly | Ser | Ile | Met<br>120 | Thr | |
| CCC | AAA | AGT | TTG | ACC | AGA | GGA | CCC | AGG | GAC | AAG | CCT | ACC | CCT | CCA | GAT | 617 |
| Pro | Lys | Ser | Leu<br>125 | Thr | Arg | Gly | Pro | Arg<br>130 | Asp | Lys | Pro | Thr | Pro<br>135 | Pro | Asp | |
| GAG | CTT | CTA | CCT | CAA | GCT | ATC | GAA | TTT | GTC | AAC | CAA | TAT | TAC | GGC | TCC | 665 |
| Glu | Leu | Leu<br>140 | Pro | Gln | Ala | Ile | Glu<br>145 | Phe | Val | Asn | Gln | Tyr<br>150 | Tyr | Gly | Ser | |
| TTC | AAA | GAG | GCA | AAA | ATA | GAG | GAA | CAT | CTG | GCC | AGG | GTG | GAA | GCG | GTA | 713 |
| Phe | Lys<br>155 | Glu | Ala | Lys | Ile | Glu<br>160 | Glu | His | Leu | Ala | Arg<br>165 | Val | Glu | Ala | Val | |
| ACA | AAG | GAG | ATA | GAA | ACA | ACA | GGA | ACC | TAC | CAA | CTG | ACG | GGA | GAT | GAG | 761 |
| Thr<br>170 | Lys | Glu | Ile | Glu | Thr<br>175 | Thr | Gly | Thr | Tyr | Gln<br>180 | Leu | Thr | Gly | Asp | Glu<br>185 | |
| CTC | ATC | TTC | GCC | ACC | AAG | CAG | GCC | TGG | CGC | AAT | GCC | CCA | CGC | TGC | ATT | 809 |
| Leu | Ile | Phe | Ala | Thr<br>190 | Lys | Gln | Ala | Trp | Arg<br>195 | Asn | Ala | Pro | Arg | Cys<br>200 | Ile | |
| GGG | AGG | ATC | CAG | TGG | TCC | AAC | CTG | CAG | GTC | TTC | GAT | GCC | CGC | AGC | TGT | 857 |
| Gly | Arg | Ile | Gln<br>205 | Trp | Ser | Asn | Leu | Gln<br>210 | Val | Phe | Asp | Ala | Arg<br>215 | Ser | Cys | |
| TCC | ACT | GCC | CGG | GAA | ATG | TTT | GAA | CAC | ATC | TGC | AGA | CAC | GTG | CGT | TAC | 905 |
| Ser | Thr | Ala<br>220 | Arg | Glu | Met | Phe | Glu<br>225 | His | Ile | Cys | Arg | His<br>230 | Val | Arg | Tyr | |
| TCC | ACC | AAC | AAT | GGC | AAC | ATC | AGG | TCG | GCC | ATC | ACC | GTG | TTC | CCC | CAG | 953 |
| Ser | Thr<br>235 | Asn | Asn | Gly | Asn | Ile<br>240 | Arg | Ser | Ala | Ile | Thr<br>245 | Val | Phe | Pro | Gln | |
| CGG | AGT | GAT | GGC | AAG | CAC | GAC | TTC | CGG | GTG | TGG | AAT | GCT | CAG | CTC | ATC | 1001 |
| Arg<br>250 | Ser | Asp | Gly | Lys | His<br>255 | Asp | Phe | Arg | Val | Trp<br>260 | Asn | Ala | Gln | Leu | Ile<br>265 | |
| CGC | TAT | GCT | GGC | TAC | CAG | ATG | CCA | GAT | GGC | AGC | ATC | AGA | GGG | GAC | CCT | 1049 |
| Arg | Tyr | Ala | Gly | Tyr<br>270 | Gln | Met | Pro | Asp | Gly<br>275 | Ser | Ile | Arg | Gly | Asp<br>280 | Pro | |
| GCC | AAC | GTG | GAA | TTC | ACT | CAG | CTG | TGC | ATC | GAC | CTG | GGC | TGG | AAG | CCC | 1097 |
| Ala | Asn | Val | Glu<br>285 | Phe | Thr | Gln | Leu | Cys<br>290 | Ile | Asp | Leu | Gly | Trp<br>295 | Lys | Pro | |
| AAG | TAC | GGC | CGC | TTC | GAT | GTG | GTC | CCC | CTG | GTC | CTG | CAG | GCC | AAT | GGC | 1145 |
| Lys | Tyr | Gly<br>300 | Arg | Phe | Asp | Val | Val<br>305 | Pro | Leu | Val | Leu | Gln<br>310 | Ala | Asn | Gly | |
| CGT | GAC | CCT | GAG | CTC | TTC | GAA | ATC | CCA | CCT | GAC | CTT | GTG | CTT | GAG | GTG | 1193 |
| Arg | Asp | Pro<br>315 | Glu | Leu | Phe | Glu<br>320 | Ile | Pro | Pro | Asp | Leu<br>325 | Val | Leu | Glu | Val | |
| GCC | ATG | GAA | CAT | CCC | AAA | TAC | GAG | TGG | TTT | CGG | GAA | CTG | GAG | CTA | AAG | 1241 |
| Ala | Met<br>330 | Glu | His | Pro | Lys<br>335 | Tyr | Glu | Trp | Phe | Arg<br>340 | Glu | Leu | Glu | Leu | Lys<br>345 | |

-continued

| | | | | | | | | | | | | | | | | |
|---|---|---|---|---|---|---|---|---|---|---|---|---|---|---|---|---|
| TGG | TAC | GCC | CTG | CCT | GCA | GTG | GCC | AAC | ATG | CTG | CTT | GAG | GTG | GGC | GGC | 1289 |
| Trp | Tyr | Ala | Leu | Pro | Ala | Val | Ala | Asn | Met | Leu | Leu | Glu | Val | Gly | Gly | |
| | | | 350 | | | | | 355 | | | | | 360 | | | |
| CTG | GAG | TTC | CCA | GGG | TGC | CCC | TTC | AAT | GGC | TGG | TAC | ATG | GGC | ACA | GAG | 1337 |
| Leu | Glu | Phe | Pro | Gly | Cys | Pro | Phe | Asn | Gly | Trp | Tyr | Met | Gly | Thr | Glu | |
| | | | 365 | | | | | 370 | | | | | 375 | | | |
| ATC | GGA | GTC | CGG | GAC | TTC | TGT | GAC | GTC | CAG | CGC | TAC | AAC | ATC | CTG | GAG | 1385 |
| Ile | Gly | Val | Arg | Asp | Phe | Cys | Asp | Val | Gln | Arg | Tyr | Asn | Ile | Leu | Glu | |
| | | | 380 | | | | | 385 | | | | | 390 | | | |
| GAA | GTG | GGC | AGG | AGA | ATG | GGC | CTG | GAA | ACG | CAC | AAG | CTG | GCC | TCG | CTC | 1433 |
| Glu | Val | Gly | Arg | Arg | Met | Gly | Leu | Glu | Thr | His | Lys | Leu | Ala | Ser | Leu | |
| | | 395 | | | | 400 | | | | | 405 | | | | | |
| TGG | AAA | GAC | CAG | GCT | GTC | GTT | GAG | ATC | AAC | ATT | GCT | GTG | ATC | CAT | AGT | 1481 |
| Trp | Lys | Asp | Gln | Ala | Val | Val | Glu | Ile | Asn | Ile | Ala | Val | Ile | His | Ser | |
| 410 | | | | | 415 | | | | | 420 | | | | | 425 | |
| TTT | CAG | AAG | CAG | AAT | GTG | ACC | ATC | ATG | GAC | CAC | CAC | TCG | GCT | GCA | GAA | 1529 |
| Phe | Gln | Lys | Gln | Asn | Val | Thr | Ile | Met | Asp | His | His | Ser | Ala | Ala | Glu | |
| | | | 430 | | | | | 435 | | | | | 440 | | | |
| TCC | TTC | ATG | AAG | TAC | ATG | CAG | AAT | GAA | TAC | CGG | TCC | CGT | GGG | GGC | TGC | 1577 |
| Ser | Phe | Met | Lys | Tyr | Met | Gln | Asn | Glu | Tyr | Arg | Ser | Arg | Gly | Gly | Cys | |
| | | | 445 | | | | | 450 | | | | | 455 | | | |
| CCG | GCA | GAC | TGG | ATT | TGG | CTG | GTC | CCT | CCC | ATG | TCT | GGG | AGC | ATC | ACC | 1625 |
| Pro | Ala | Asp | Trp | Ile | Trp | Leu | Val | Pro | Pro | Met | Ser | Gly | Ser | Ile | Thr | |
| | | 460 | | | | 465 | | | | | 470 | | | | | |
| CCC | GTG | TTT | CAC | CAG | GAG | ATG | CTG | AAC | TAC | GTC | CTG | TCC | CCT | TTC | TAC | 1673 |
| Pro | Val | Phe | His | Gln | Glu | Met | Leu | Asn | Tyr | Val | Leu | Ser | Pro | Phe | Tyr | |
| | 475 | | | | | 480 | | | | | 485 | | | | | |
| TAC | TAT | CAG | GTA | GAG | GCC | TGG | AAA | ACC | CAT | GTC | TGG | CAG | GAC | GAG | AAG | 1721 |
| Tyr | Tyr | Gln | Val | Glu | Ala | Trp | Lys | Thr | His | Val | Trp | Gln | Asp | Glu | Lys | |
| 490 | | | | | 495 | | | | | 500 | | | | | 505 | |
| CGG | AGA | CCC | AAG | AGA | AGA | GAG | ATT | CCA | TTG | AAA | GTC | TTG | GTC | AAA | GCT | 1769 |
| Arg | Arg | Pro | Lys | Arg | Arg | Glu | Ile | Pro | Leu | Lys | Val | Leu | Val | Lys | Ala | |
| | | | | 510 | | | | | 515 | | | | | 520 | | |
| GTG | CTC | TTT | GCC | TGT | ATG | CTG | ATG | CGC | AAG | ACA | ATG | GCG | TCC | CGA | GTC | 1817 |
| Val | Leu | Phe | Ala | Cys | Met | Leu | Met | Arg | Lys | Thr | Met | Ala | Ser | Arg | Val | |
| | | | 525 | | | | | 530 | | | | | 535 | | | |
| AGA | GTC | ACC | ATC | CTC | TTT | GCG | ACA | GAG | ACA | GGA | AAA | TCA | GAG | GCG | CTG | 1865 |
| Arg | Val | Thr | Ile | Leu | Phe | Ala | Thr | Glu | Thr | Gly | Lys | Ser | Glu | Ala | Leu | |
| | | 540 | | | | 545 | | | | | 550 | | | | | |
| GCC | TGG | GAC | CTG | GGG | GCC | TTA | TTC | AGC | TGT | GCC | TTC | AAC | CCC | AAG | GTT | 1913 |
| Ala | Trp | Asp | Leu | Gly | Ala | Leu | Phe | Ser | Cys | Ala | Phe | Asn | Pro | Lys | Val | |
| | 555 | | | | | 560 | | | | | 565 | | | | | |
| GTC | TGC | ATG | GAT | AAG | TAC | AGG | CTG | AGC | TGC | CTG | GAG | GAG | GAA | CGG | CTG | 1961 |
| Val | Cys | Met | Asp | Lys | Tyr | Arg | Leu | Ser | Cys | Leu | Glu | Glu | Glu | Arg | Leu | |
| 570 | | | | | 575 | | | | | 580 | | | | | 585 | |
| CTG | TTG | GTG | GTG | ACC | AGT | ACG | TTT | GGC | AAT | GGA | GAC | TGC | CCT | GGC | AAT | 2009 |
| Leu | Leu | Val | Val | Thr | Ser | Thr | Phe | Gly | Asn | Gly | Asp | Cys | Pro | Gly | Asn | |
| | | | | 590 | | | | | 595 | | | | | 600 | | |
| GGA | GAG | AAA | CTG | AAG | AAA | TCG | CTC | TTC | ATG | CTG | AAA | GAG | CTC | AAC | AAC | 2057 |
| Gly | Glu | Lys | Leu | Lys | Lys | Ser | Leu | Phe | Met | Leu | Lys | Glu | Leu | Asn | Asn | |
| | | | | 605 | | | | | 610 | | | | | 615 | | |
| AAA | TTC | AGG | TAC | GCT | GTG | TTT | GGC | CTC | GGC | TCC | AGC | ATG | TAC | CCT | CGG | 2105 |
| Lys | Phe | Arg | Tyr | Ala | Val | Phe | Gly | Leu | Gly | Ser | Ser | Met | Tyr | Pro | Arg | |
| | | 620 | | | | 625 | | | | | 630 | | | | | |
| TTC | TGC | GCC | TTT | GCT | CAT | GAC | ATT | GAT | CAG | AAG | CTG | TCC | CAC | CTG | GGG | 2153 |
| Phe | Cys | Ala | Phe | Ala | His | Asp | Ile | Asp | Gln | Lys | Leu | Ser | His | Leu | Gly | |
| | 635 | | | | | 640 | | | | | 645 | | | | | |
| GCC | TCT | CAG | CTC | ACC | CCG | ATG | GGA | GAA | GGG | GAT | GAG | CTC | AGT | GGG | CAG | 2201 |
| Ala | Ser | Gln | Leu | Thr | Pro | Met | Gly | Glu | Gly | Asp | Glu | Leu | Ser | Gly | Gln | |
| 650 | | | | | 655 | | | | | 660 | | | | | 665 | |

```
GAG GAC GCC TTC CGC AGC TGG GCC GTG CAA ACC TTC AAG GCA GCC TGT    2249
Glu Asp Ala Phe Arg Ser Trp Ala Val Gln Thr Phe Lys Ala Ala Cys
                670             675                 680

GAG ACG TTT GAT GTC CGA GGC AAA CAG CAC ATT CAG ATC CCC AAG CTC    2297
Glu Thr Phe Asp Val Arg Gly Lys Gln His Ile Gln Ile Pro Lys Leu
            685             690                 695

TAC ACC TCC AAT GTG ACC TGG GAC CCG CAC CAC TAC AGG CTC GTG CAG    2345
Tyr Thr Ser Asn Val Thr Trp Asp Pro His His Tyr Arg Leu Val Gln
        700             705                 710

GAC TCA CAG CCT TTG GAC CTC AGC AAA GCC CTC AGC AGC ATG CAT GCC    2393
Asp Ser Gln Pro Leu Asp Leu Ser Lys Ala Leu Ser Ser Met His Ala
    715             720             725

AAG AAC GTG TTC ACC ATG AGG CTC AAA TCT CGG CAG AAT CTA CAA AGT    2441
Lys Asn Val Phe Thr Met Arg Leu Lys Ser Arg Gln Asn Leu Gln Ser
730             735             740                 745

CCG ACA TCC AGC CGT GCC ACC ATC CTG GTG GAA CTC TCC TGT GAG GAT    2489
Pro Thr Ser Ser Arg Ala Thr Ile Leu Val Glu Leu Ser Cys Glu Asp
                750             755                 760

GGC CAA GGC CTG AAC TAC CTG CCG GGG GAG CAC CTT GGG GTT TGC CCA    2537
Gly Gln Gly Leu Asn Tyr Leu Pro Gly Glu His Leu Gly Val Cys Pro
            765             770                 775

GGC AAC CAG CCG GCC CTG GTC CAA GGC ATC CTG GAG CGA GTG GTG GAT    2585
Gly Asn Gln Pro Ala Leu Val Gln Gly Ile Leu Glu Arg Val Val Asp
        780             785                 790

GGC CCC ACA CCC CAC CAG ACA GTG CGC CTG GAG GAC CTG GAT GAG AGT    2633
Gly Pro Thr Pro His Gln Thr Val Arg Leu Glu Asp Leu Asp Glu Ser
    795             800             805

GGC AGC TAC TGG GTC AGT GAC AAG AGG CTG CCC CCC TGC TCA CTC AGC    2681
Gly Ser Tyr Trp Val Ser Asp Lys Arg Leu Pro Pro Cys Ser Leu Ser
810             815             820             825

CAG GCC CTC ACC TAC TCC CCG GAC ATC ACC ACA CCC CCA ACC CAG CTG    2729
Gln Ala Leu Thr Tyr Ser Pro Asp Ile Thr Thr Pro Pro Thr Gln Leu
                830             835                 840

CTG CTC CAA AAG CTG GCC CAG GTG GCC ACA GAA GAG CCT GAG AGA CAG    2777
Leu Leu Gln Lys Leu Ala Gln Val Ala Thr Glu Glu Pro Glu Arg Gln
            845             850                 855

AGG CTG GAG GCC CTG TGC CAG CCC TCA GAG TAC AGC AAG TGG AAG TTC    2825
Arg Leu Glu Ala Leu Cys Gln Pro Ser Glu Tyr Ser Lys Trp Lys Phe
        860             865                 870

ACC AAC AGC CCC ACA TTC CTG GAG GTG CTA GAG GAG TTC CCG TCC CTG    2873
Thr Asn Ser Pro Thr Phe Leu Glu Val Leu Glu Glu Phe Pro Ser Leu
    875             880             885

CGG GTG TCT GCT GGC TTC CTG CTT TCC CAG CTC CCC ATT CTG AAG CCC    2921
Arg Val Ser Ala Gly Phe Leu Leu Ser Gln Leu Pro Ile Leu Lys Pro
890             895             900             905

AGG TTC TAC TCC ATC AGC TCC TCC CGG GAT CAC ACG CCC ACG GAG ATC    2969
Arg Phe Tyr Ser Ile Ser Ser Ser Arg Asp His Thr Pro Thr Glu Ile
                910             915                 920

CAC CTG ACT GTG GCC GTG GTC ACC TAC CAC ACC GGA GAT GGC CAG GGT    3017
His Leu Thr Val Ala Val Val Thr Tyr His Thr Gly Asp Gly Gln Gly
            925             930                 935

CCC CTG CAC CAC GGT GTC TGC AGC ACA TGG CTC AAC AGC CTG AAG CCC    3065
Pro Leu His His Gly Val Cys Ser Thr Trp Leu Asn Ser Leu Lys Pro
        940             945                 950

CAA GAC CCA GTG CCC TGC TTT GTG CGG AAT GCC AGC GCC TTC CAC CTC    3113
Gln Asp Pro Val Pro Cys Phe Val Arg Asn Ala Ser Ala Phe His Leu
    955             960             965

CCC GAG GAT CCC TCC CAT CCT TGC ATC CTC ATC GGG CCT GGC ACA GGC    3161
Pro Glu Asp Pro Ser His Pro Cys Ile Leu Ile Gly Pro Gly Thr Gly
```

| | | | | | | | | | | | | | | | | |
|---|---|---|---|---|---|---|---|---|---|---|---|---|---|---|---|---|
| | 970 | | | | 975 | | | | | 980 | | | | 985 | | |
| ATC | GTG | CCC | TTC | CGC | AGT | TTC | TGG | CAG | CAA | CGG | CTC | CAT | GAC | TCC | CAG | 3209 |
| Ile | Val | Pro | Phe | Arg | Ser | Phe | Trp | Gln | Gln | Arg | Leu | His | Asp | Ser | Gln | |
| | | | | 990 | | | | | 995 | | | | | 1000 | | |
| CAC | AAG | GGA | GTG | CGG | GGA | GGC | CGC | ATG | ACC | TTG | GTG | TTT | GGG | TGC | CGC | 3257 |
| His | Lys | Gly | Val | Arg | Gly | Gly | Arg | Met | Thr | Leu | Val | Phe | Gly | Cys | Arg | |
| | | | | 1005 | | | | | 1010 | | | | | 1015 | | |
| CGC | CCA | GAT | GAG | GAC | CAC | ATC | TAC | CAG | GAG | GAG | ATG | CTG | GAG | ATG | GCC | 3305 |
| Arg | Pro | Asp | Glu | Asp | His | Ile | Tyr | Gln | Glu | Glu | Met | Leu | Glu | Met | Ala | |
| | | | 1020 | | | | | 1025 | | | | | 1030 | | | |
| CAG | AAG | GGG | GTG | CTG | CAT | GCG | GTG | CAC | ACA | GCC | TAT | TCC | CGC | CTG | CCT | 3353 |
| Gln | Lys | Gly | Val | Leu | His | Ala | Val | His | Thr | Ala | Tyr | Ser | Arg | Leu | Pro | |
| | | 1035 | | | | | 1040 | | | | | 1045 | | | | |
| GGC | AAG | CCC | AAG | GTC | TAT | GTT | CAG | GAC | ATC | CTG | CGG | CAG | CAG | CTG | GCC | 3401 |
| Gly | Lys | Pro | Lys | Val | Tyr | Val | Gln | Asp | Ile | Leu | Arg | Gln | Gln | Leu | Ala | |
| 1050 | | | | | 1055 | | | | | 1060 | | | | | 1065 | |
| AGC | GAG | GTG | CTC | CGT | GTG | CTC | CAC | AAG | GAG | CCA | GGC | CAC | CTC | TAT | GTT | 3449 |
| Ser | Glu | Val | Leu | Arg | Val | Leu | His | Lys | Glu | Pro | Gly | His | Leu | Tyr | Val | |
| | | | | 1070 | | | | | 1075 | | | | | 1080 | | |
| TGC | GGG | GAT | GTG | CGC | ATG | GCC | CGG | GAC | GTG | GCC | CAC | ACC | CTG | AAG | CAG | 3497 |
| Cys | Gly | Asp | Val | Arg | Met | Ala | Arg | Asp | Val | Ala | His | Thr | Leu | Lys | Gln | |
| | | | 1085 | | | | | 1090 | | | | | 1095 | | | |
| CTG | GTG | GCT | GCC | AAG | CTG | AAA | TTG | AAT | GAG | GAG | CAG | GTC | GAG | GAC | TAT | 3545 |
| Leu | Val | Ala | Ala | Lys | Leu | Lys | Leu | Asn | Glu | Glu | Gln | Val | Glu | Asp | Tyr | |
| | | | 1100 | | | | | 1105 | | | | | 1110 | | | |
| TTC | TTT | CAG | CTC | AAG | AGC | CAG | AAG | CGC | TAT | CAC | GAA | GAT | ATC | TTC | GGT | 3593 |
| Phe | Phe | Gln | Leu | Lys | Ser | Gln | Lys | Arg | Tyr | His | Glu | Asp | Ile | Phe | Gly | |
| | | 1115 | | | | | 1120 | | | | | 1125 | | | | |
| GCT | GTA | TTT | CCT | TAC | GAG | GCG | AAG | AAG | GAC | AGG | GTG | GCG | GTG | CAG | CCC | 3641 |
| Ala | Val | Phe | Pro | Tyr | Glu | Ala | Lys | Lys | Asp | Arg | Val | Ala | Val | Gln | Pro | |
| 1130 | | | | | 1135 | | | | | 1140 | | | | | 1145 | |
| AGC | AGC | CTG | GAG | ATG | TCA | GCG | CTC | TGAGGGCCTA | | CAGGAGGGGT | | TAAAGCTGCC | | | | 3695 |
| Ser | Ser | Leu | Glu | Met | Ser | Ala | Leu | | | | | | | | | |
| | | | | 1150 | | | | | | | | | | | | |

| | | | | | |
|---|---|---|---|---|---|
| GGCACAGAAC | TTAAGGATGG | AGCCAGCTCT | GCATTATCTG | AGGTCACAGG | GCCTGGGGAG | 3755 |
| ATGGAGGAAA | GTGATATCCC | CCAGCCTCAA | GTCTTATTTC | CTCAACGTTG | CTCCCCATCA | 3815 |
| AGCCCTTTAC | TTGACCTCCT | AACAAGTAGC | ACCCTGGATT | GATCGGAGCC | TCCTCTCTCA | 3875 |
| AACTGGGGCC | TCCCTGGTCC | CTTGGAGACA | AAATCTTAAA | TGCCAGGCCT | GGCGAGTGGG | 3935 |
| TGAAAGATGG | AACTTGCTGC | TGAGTGCACC | ACTTCAAGTG | ACCACCAGGA | GGTGCTATCG | 3995 |
| CACCACTGTG | TATTTAACTG | CCTTGTGTAC | AGTTATTTAT | GCCTCTGTAT | TTAAAAAACT | 4055 |
| AACACCCAGT | CTGTTCCCCA | TGGCCACTTG | GGTCTTCCCT | GTATGATTCC | TTGATGGAGA | 4115 |
| TATTTACATG | AATTGCATTT | TACTTTAATC | | | | 4145 |

( 2 ) INFORMATION FOR SEQ ID NO:2:

( i ) SEQUENCE CHARACTERISTICS:
        ( A ) LENGTH: 1153 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Cys | Pro | Trp | Lys | Phe | Leu | Phe | Lys | Thr | Lys | Phe | His | Gln | Tyr |
| 1 | | | | 5 | | | | | 10 | | | | | 15 | |
| Ala | Met | Asn | Gly | Glu | Lys | Asp | Ile | Asn | Asn | Val | Glu | Lys | Ala | Pro | |
| | | | 20 | | | | | 25 | | | | | 30 | | |

|     |     |     |     |     |     |     |     |     |     |     |     |     |     |     |
|-----|-----|-----|-----|-----|-----|-----|-----|-----|-----|-----|-----|-----|-----|-----|
| Cys | Ala | Thr 35 | Ser | Ser | Pro | Val | Thr 40 | Gln | Asp | Asp | Leu | Gln 45 | Tyr | His | Asn |
| Leu | Ser 50 | Lys | Gln | Gln | Asn | Ser 55 | Pro | Gln | Pro | Leu 60 | Val | Glu | Thr | Gly |
| Lys 65 | Lys | Ser | Pro | Glu | Ser 70 | Leu | Val | Lys | Leu | Asp 75 | Ala | Thr | Pro | Leu | Ser 80 |
| Ser | Pro | Arg | His | Val 85 | Arg | Ile | Lys | Asn | Trp 90 | Gly | Ser | Gly | Met | Thr 95 | Phe |
| Gln | Asp | Thr | Leu 100 | His | His | Lys | Ala | Lys 105 | Gly | Ile | Leu | Thr | Cys 110 | Arg | Ser |
| Lys | Ser | Cys 115 | Leu | Gly | Ser | Ile | Met 120 | Thr | Pro | Lys | Ser | Leu 125 | Thr | Arg | Gly |
| Pro | Arg 130 | Asp | Lys | Pro | Thr | Pro 135 | Pro | Asp | Glu | Leu | Leu 140 | Pro | Gln | Ala | Ile |
| Glu 145 | Phe | Val | Asn | Gln | Tyr 150 | Tyr | Gly | Ser | Phe | Lys 155 | Glu | Ala | Lys | Ile | Glu 160 |
| Glu | His | Leu | Ala | Arg 165 | Val | Glu | Ala | Val | Thr 170 | Lys | Glu | Ile | Glu | Thr 175 | Thr |
| Gly | Thr | Tyr | Gln 180 | Leu | Thr | Gly | Asp | Glu 185 | Leu | Ile | Phe | Ala | Thr 190 | Lys | Gln |
| Ala | Trp | Arg 195 | Asn | Ala | Pro | Arg | Cys 200 | Ile | Gly | Arg | Ile | Gln 205 | Trp | Ser | Asn |
| Leu | Gln 210 | Val | Phe | Asp | Ala | Arg 215 | Ser | Cys | Ser | Thr | Ala 220 | Arg | Glu | Met | Phe |
| Glu 225 | His | Ile | Cys | Arg | His 230 | Val | Arg | Tyr | Ser | Thr 235 | Asn | Asn | Gly | Asn | Ile 240 |
| Arg | Ser | Ala | Ile | Thr 245 | Val | Phe | Pro | Gln | Arg 250 | Ser | Asp | Gly | Lys | His 255 | Asp |
| Phe | Arg | Val | Trp 260 | Asn | Ala | Gln | Leu | Ile 265 | Arg | Tyr | Ala | Gly | Tyr 270 | Gln | Met |
| Pro | Asp | Gly 275 | Ser | Ile | Arg | Gly | Asp 280 | Pro | Ala | Asn | Val | Glu 285 | Phe | Thr | Gln |
| Leu | Cys 290 | Ile | Asp | Leu | Gly | Trp 295 | Lys | Pro | Lys | Tyr | Gly 300 | Arg | Phe | Asp | Val |
| Val 305 | Pro | Leu | Val | Leu | Gln 310 | Ala | Asn | Gly | Arg | Asp 315 | Pro | Glu | Leu | Phe | Glu 320 |
| Ile | Pro | Pro | Asp | Leu 325 | Val | Leu | Glu | Val | Ala 330 | Met | Glu | His | Pro | Lys 335 | Tyr |
| Glu | Trp | Phe | Arg 340 | Glu | Leu | Glu | Leu | Lys 345 | Trp | Tyr | Ala | Leu | Pro 350 | Ala | Val |
| Ala | Asn | Met 355 | Leu | Leu | Glu | Val | Gly 360 | Gly | Leu | Glu | Phe | Pro 365 | Gly | Cys | Pro |
| Phe | Asn 370 | Gly | Trp | Tyr | Met | Gly 375 | Thr | Glu | Ile | Gly | Val 380 | Arg | Asp | Phe | Cys |
| Asp 385 | Val | Gln | Arg | Tyr | Asn 390 | Ile | Leu | Glu | Glu | Val 395 | Gly | Arg | Arg | Met | Gly 400 |
| Leu | Glu | Thr | His | Lys 405 | Leu | Ala | Ser | Leu | Trp 410 | Lys | Asp | Gln | Ala | Val 415 | Val |
| Glu | Ile | Asn | Ile 420 | Ala | Val | Ile | His | Ser 425 | Phe | Gln | Lys | Gln | Asn 430 | Val | Thr |
| Ile | Met | Asp 435 | His | His | Ser | Ala | Ala 440 | Glu | Ser | Phe | Met | Lys 445 | Tyr | Met | Gln |

| | | | | | | | | | | | | | | |
|---|---|---|---|---|---|---|---|---|---|---|---|---|---|---|
| Asn | Glu 450 | Tyr | Arg | Ser | Arg | Gly 455 | Gly | Cys | Pro | Ala | Asp 460 | Trp | Ile | Trp | Leu |
| Val 465 | Pro | Pro | Met | Ser | Gly 470 | Ser | Ile | Thr | Pro | Val 475 | Phe | His | Gln | Glu | Met 480 |
| Leu | Asn | Tyr | Val | Leu 485 | Ser | Pro | Phe | Tyr | Tyr 490 | Tyr | Gln | Val | Glu | Ala 495 | Trp |
| Lys | Thr | His | Val 500 | Trp | Gln | Asp | Glu | Lys 505 | Arg | Arg | Pro | Lys | Arg 510 | Arg | Glu |
| Ile | Pro | Leu | Lys 515 | Val | Leu | Val | Lys 520 | Ala | Val | Leu | Phe | Ala 525 | Cys | Met | Leu |
| Met | Arg 530 | Lys | Thr | Met | Ala | Ser 535 | Arg | Val | Arg | Val | Thr 540 | Ile | Leu | Phe | Ala |
| Thr 545 | Glu | Thr | Gly | Lys | Ser 550 | Glu | Ala | Leu | Ala | Trp 555 | Asp | Leu | Gly | Ala | Leu 560 |
| Phe | Ser | Cys | Ala | Phe 565 | Asn | Pro | Lys | Val | Val 570 | Cys | Met | Asp | Lys | Tyr 575 | Arg |
| Leu | Ser | Cys | Leu 580 | Glu | Glu | Glu | Arg | Leu 585 | Leu | Val | Val | Thr | Ser 590 | Thr |
| Phe | Gly | Asn 595 | Gly | Asp | Cys | Pro | Gly 600 | Asn | Gly | Glu | Lys | Leu 605 | Lys | Lys | Ser |
| Leu | Phe 610 | Met | Leu | Lys | Glu | Leu 615 | Asn | Asn | Lys | Phe | Arg 620 | Tyr | Ala | Val | Phe |
| Gly 625 | Leu | Gly | Ser | Ser | Met 630 | Tyr | Pro | Arg | Phe | Cys 635 | Ala | Phe | Ala | His | Asp 640 |
| Ile | Asp | Gln | Lys | Leu 645 | Ser | His | Leu | Gly | Ala 650 | Ser | Gln | Leu | Thr | Pro 655 | Met |
| Gly | Glu | Gly | Asp 660 | Glu | Leu | Ser | Gly | Gln 665 | Glu | Asp | Ala | Phe | Arg 670 | Ser | Trp |
| Ala | Val | Gln 675 | Thr | Phe | Lys | Ala | Ala 680 | Cys | Glu | Thr | Phe | Asp 685 | Val | Arg | Gly |
| Lys | Gln 690 | His | Ile | Gln | Ile | Pro 695 | Lys | Leu | Tyr | Thr | Ser 700 | Asn | Val | Thr | Trp |
| Asp 705 | Pro | His | His | Tyr | Arg 710 | Leu | Val | Gln | Asp | Ser 715 | Gln | Pro | Leu | Asp | Leu 720 |
| Ser | Lys | Ala | Leu | Ser 725 | Ser | Met | His | Ala | Lys 730 | Asn | Val | Phe | Thr | Met 735 | Arg |
| Leu | Lys | Ser | Arg 740 | Gln | Asn | Leu | Gln | Ser 745 | Pro | Thr | Ser | Ser | Arg 750 | Ala | Thr |
| Ile | Leu | Val 755 | Glu | Leu | Ser | Cys | Glu 760 | Asp | Gly | Gln | Gly | Leu 765 | Asn | Tyr | Leu |
| Pro | Gly 770 | Glu | His | Leu | Gly | Val 775 | Cys | Pro | Gly | Asn | Gln 780 | Pro | Ala | Leu | Val |
| Gln 785 | Gly | Ile | Leu | Glu | Arg 790 | Val | Val | Asp | Gly | Pro 795 | Thr | Pro | His | Gln | Thr 800 |
| Val | Arg | Leu | Glu | Asp 805 | Leu | Asp | Glu | Ser | Gly 810 | Ser | Tyr | Trp | Val | Ser 815 | Asp |
| Lys | Arg | Leu | Pro 820 | Pro | Cys | Ser | Leu | Ser 825 | Gln | Ala | Leu | Thr | Tyr 830 | Ser | Pro |
| Asp | Ile | Thr 835 | Thr | Pro | Pro | Thr | Gln 840 | Leu | Leu | Leu | Gln | Lys 845 | Leu | Ala | Gln |
| Val | Ala 850 | Thr | Glu | Glu | Pro | Glu 855 | Arg | Gln | Arg | Leu | Glu 860 | Ala | Leu | Cys | Gln |
| Pro | Ser | Glu | Tyr | Ser | Lys | Trp | Lys | Phe | Thr | Asn | Ser | Pro | Thr | Phe | Leu |

|     | 865 |     |     | 870 |     |     |     |     | 875 |     |     |     |     | 880 |
|-----|-----|-----|-----|-----|-----|-----|-----|-----|-----|-----|-----|-----|-----|-----|
| Glu | Val | Leu | Glu | Glu 885 | Phe | Pro | Ser | Leu | Arg 890 | Val | Ser | Ala | Gly | Phe 895 | Leu |

Leu Ser Gln Leu Pro Ile Leu Lys Pro Arg Phe Tyr Ser Ile Ser Ser
          900                 905                     910

Ser Arg Asp His Thr Pro Thr Glu Ile His Leu Thr Val Ala Val Val
        915                 920                 925

Thr Tyr His Thr Gly Asp Gly Gln Gly Pro Leu His His Gly Val Cys
    930             935                 940

Ser Thr Trp Leu Asn Ser Leu Lys Pro Gln Asp Pro Val Pro Cys Phe
945             950                 955                     960

Val Arg Asn Ala Ser Ala Phe His Leu Pro Glu Asp Pro Ser His Pro
                965             970                     975

Cys Ile Leu Ile Gly Pro Gly Thr Gly Ile Val Pro Phe Arg Ser Phe
            980             985                 990

Trp Gln Gln Arg Leu His Asp Ser Gln His Lys Gly Val Arg Gly Gly
        995             1000                1005

Arg Met Thr Leu Val Phe Gly Cys Arg Arg Pro Asp Glu Asp His Ile
    1010            1015                1020

Tyr Gln Glu Glu Met Leu Glu Met Ala Gln Lys Gly Val Leu His Ala
1025            1030                1035                1040

Val His Thr Ala Tyr Ser Arg Leu Pro Gly Lys Pro Lys Val Tyr Val
            1045                1050                1055

Gln Asp Ile Leu Arg Gln Gln Leu Ala Ser Glu Val Leu Arg Val Leu
            1060            1065                1070

His Lys Glu Pro Gly His Leu Tyr Val Cys Gly Asp Val Arg Met Ala
        1075            1080                1085

Arg Asp Val Ala His Thr Leu Lys Gln Leu Val Ala Ala Lys Leu Lys
    1090            1095                1100

Leu Asn Glu Glu Gln Val Glu Asp Tyr Phe Phe Gln Leu Lys Ser Gln
1105            1110                1115                1120

Lys Arg Tyr His Glu Asp Ile Phe Gly Ala Val Phe Pro Tyr Glu Ala
            1125                1130                1135

Lys Lys Asp Arg Val Ala Val Gln Pro Ser Ser Leu Glu Met Ser Ala
        1140            1145                1150

Leu

CDNA CLONE FOR HUMAN INDUCIBLE NITRIC OXIDE SYNTHASE AND PROCESS FOR PREPARING SAME

BACKGROUND OF THE INVENTION

The invention described herein was made in the course of work supported in part by Public Health Service, Grant Nos. GM44100 and GM37753 from the National Institutes of Health, General Medical Sciences. This is a continuation of application Ser. No. 07/981,344, filed Nov. 25, 1992 now abandoned.

The following microorganisms have been deposited by David A. Geller on behalf of the University of Pittsburgh of the Commonwealth System of Higher Education, Pittsburgh, Pa. 15260, USA, on Nov. 18, 1992, with and are available from the permanent collection of the American Type Culture Collection (ATCC), 12301 Parklawn Drive, Rockville, Md. 202852-1776, USA:

ATCC 75358 Human Hepatocyte inducible Nitric Oxide Synthase cDNA in pBluescript (pHINOS)

ATCC 69126 Human Hepatocyte Inducible Nitric Oxide Synthase cDNA in pBluescript transformed in *E. coli* SOLR bacteria (plasmid HINOS cDNA)

The American Type Culture Collection has performed viability tests on each of the hereinbefore mentioned deposited microorganisms and has concluded on Nov. 20, 1992, that each of the hereinbefore mentioned deposited microorganisms is viable and capable of reproduction.

These deposits are available to the public upon the grant of a patent to the assignee, the University of Pittsburgh of the Commonwealth System of Higher Education, disclosing them. However, it should be understood that the availability of these deposits does not constitute a license to practice this invention in derogation of patent rights granted by governmental action.

FIELD OF THE INVENTION

This invention relates to a human tissue inducible nitric oxide synthase cDNA clone capable of expressing a human inducible nitric oxide synthase protein, and a process suitable for cloning a cDNA encoding amino acid sequences for the human inducible nitric oxide synthase. More specifically, this invention relates to a human hepatocyte inducible nitric oxide synthase cDNA clone and to a process for cloning and expression of the human hepatocyte inducible nitric oxide synthase cDNA to provide a source of the human hepatocyte inducible nitric oxide synthase enzyme.

This invention provides a process for cloning a cDNA having an amino acid sequence coding for the human hepatocyte inducible nitric oxide synthase. FIGS. 1A–G show and SEQ ID NO: 1 in the SEQUENCE LISTING contains the 4,145 nucleotide bases for the sense strand of cDNA for human hepatocyte inducible nitric oxide synthase and sets forth the base codes as triplets (codon) for the coding parts of the nucleotide sequence. FIGS. 1A–G snow and SEQ ID NOS: 1 and 2 sets forth the amino acid sequence for the cDNA clone for human hepatocyte inducible nitric oxide synthase encoding amino acids 1 through 1153 of the human hepatocyte inducible nitric oxide synthase enzyme.

BRIEF DESCRIPTION OF BACKGROUND ART

It is known by those skilled in the art that nitric oxide (NO) is a biologic mediator derived from the amino acid L-arginine. One of a family of enzymes, nitric oxide synthase (NOS), acts upon L-arginine to oxidize one of the guanidino nitrogens to NO while citrulline is formed from the remainder of the L-arginine molecule. Nitric oxide is a very short-lived free radical and is rapidly oxidized to nitrite ($NO_2^-$) and nitrate ($NO_3^-$) which is measured as the stable inactive end products of nitric oxide formation.

It is well known by those skilled in the art that multiple isoforms of the nitric oxide synthase enzyme exist and that they are generally classified into two broad categories: 1) constitutive and 2) inducible. These classes of NOS enzymes vary considerably in their size, amino acid sequence, activity and regulation. For example, cells such as neurons and vascular endothelial cells contain constitutive NOS isotypes while macrophages and vascular smooth muscle cells express an inducible NOS.

it is generally well known that small amounts of NO generated by a constitutive NOS appear to act as a messenger molecule by activating soluble guanylate cyclase and, thus, increasing intracellular guanosine, 3', 5'-cyclic monophosphate (cGMP) and the induction of biological responses that are dependent on cGMP as a secondary messenger. For example, through this mechanism, endothelial derived NO induces relaxation of vascular smooth muscle and is identified as endothelium derived relaxing factor (EDRF). *Nature*, Vol. 327, pp. 524–526 (1987) and *Proc Natl. Acad Sci USA*, Vol. 84, pp. 9265–9269 (1987). Another example includes, but is not limited by, neuronal nitric oxide which acts as a neuro transmitter by activating guanylate cyclase with important functions in the central nervous system and autonomic nervous systems. *Proc Natl Acad Sci USA*, Vol. 86, pp. 9030–9033 (1989) and *Science*, Vol. 257, p. 401 (1992).

It is generally known by those skilled in the art that the larger quantities of nitric oxide produced by the inducible nitric oxide synthase have antimicrobial and antitumor functions. *J. Clin. Invest.*, Vol 81, pp. 1129–1136 (1989) and *Science*, Vol. 235, pp. 473–476 (1987), respectively. It is also known by those skilled in the art that when vascular smooth muscle cells are stimulated to express a NOS enzyme by inflammatory cytokines, the excess amounts of nitric oxides that are produced contribute to the vascular collapse seen in sepsis. *FEBS Lett.*, Vol. 265, pp. 133–136, (1990).

Thus, it will be appreciated that nitric oxide has both normal physiologic intracellular and extracellular regulatory functions. However, excessive production of nitric oxide is detrimental. For example, stimulation of inducible nitric oxide synthesis in blood vessels by bacterial endotoxin such as for example bacterial lipopolysaccharide (LPS) and cytokines that are elevated in sepsis results in massive dilation of blood vessels and sustained hypotension commonly encountered in septic shock. *Proc. Natl. Acad. Sci USA*, Vol. 87, pp. 3629–32 (1990). It is known that overproduction of nitric oxide in the lungs stimulated by immune complexes directly damages the lung. *J. Immunol.*, Vol. 148, p. 3086 (1992). Induction of nitric oxide synthase in pancreatic islets impairs insulin secretion and contributes to the onset of juvenile diabetes. *J. Biol. Chem.*, Vol. 266, p. 21351 (1991).

It will be appreciated that there is a great need in the medical community for collective inhibition of the inducible form of NOS but not the constitutive types of NOS in humans because this would allow for a means of preventing, such as for example, the hypotensive shock seen in sepsis, without preventing the physiologic regulation of vasomotor tone or neuro transmission in the central nervous system.

We recently demonstrated that nitric oxide biosynthesis is induced in isolated human hepatocytes after stimulation with interleukin-1, tumor necrosis factor-alpha, interferon-gamma and bacterial lipopolysacharride (bacterial endotoxin). *FASEB JOURNAL*, Vol. 6, No. 5, page A1834 (April, 1992) and *J. Exp. Med.*, Vol. 176, p. 261 (1992). Heretofore no human cell type was known to show increased production of nitrogen oxides when treated with cytokines. *Res. Immunol.*, Vol. 142, p. 557 (1991). It is generally known by those skilled in the art that all attempts to induce nitric oxide synthase in human macrophages and related cells typical to those found in rodent macrophages have failed. *Res. immunol.*, Vol. 142, p. 562, 589–90 (1991).

In spite of this background material, there remains a very real and substantial need for a cDNA clone for human tissue inducible nitric oxide synthase and a process for the molecular cloning of the same.

BRIEF DESCRIPTION OF THE DRAWINGS

FIGS. 1A–G collectively show the cDNA sense sequence (top line of each horizontal row) and the amino acid sequence of amino acids 1–1153 (bottom line of each horizontal row) for the cDNA clone for human hepatocyte inducible nitric oxide synthase, SEQ ID NO: 1.

SUMMARY OF THE INVENTION

Figure 2:
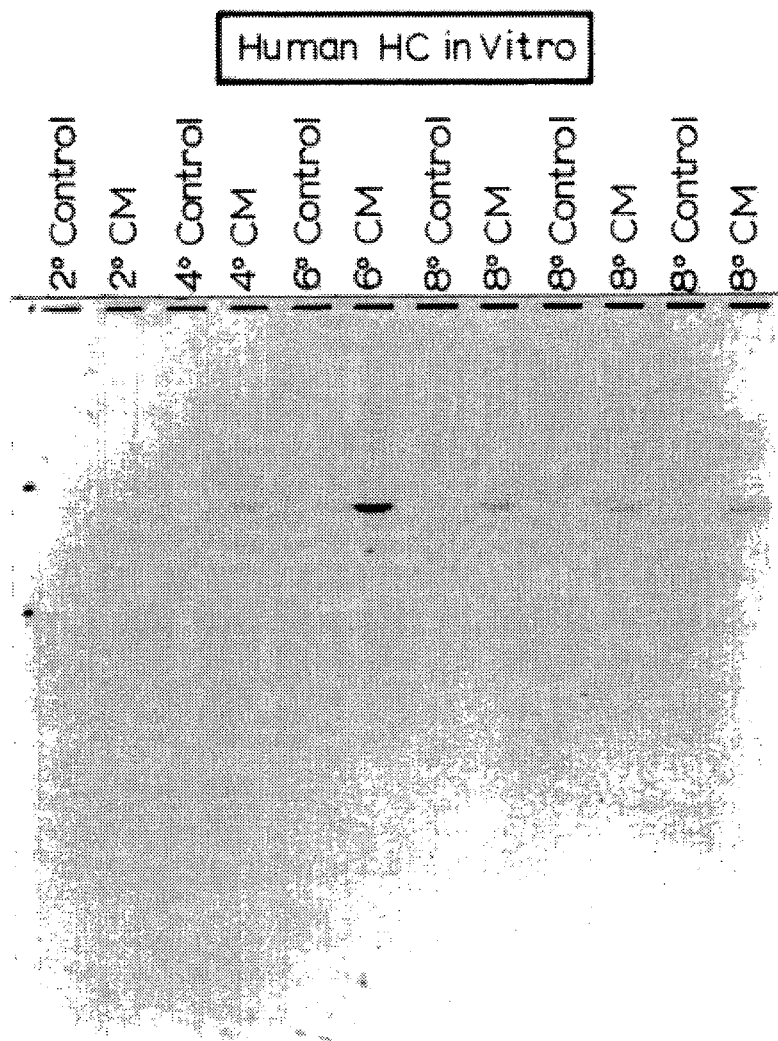
FIG. 2 shows a Northern Blot of a mouse macrophage NOS cDNA cross-hybridizing to human hepatocyte (HC) nitric oxide synthase mRNA.

The present invention has met the hereinbefore described needs. The present invention provides a cDNA clone for human tissue inducible nitric oxide synthase and a process for preparing the same.

More specifically, this invention provides a cDNA clone for human hepatocyte inducible nitric oxide synthase and a process for preparing the same. This process includes inducing nitric oxide synthase in human hepatocytes, identifying human hepatocyte nitric oxide synthase messenger RNA, isolating the human hepatocyte nitric oxide synthase messenger RNA, collecting the human hepatocyte nitric oxide synthase messenger RNA, separating human hepatocyte poly A messenger RNA from the human hepatocyte nitric oxide synthase messenger RNA, constructing a cDNA library for human hepatocyte nitric oxide synthase, screening this cDNA library for human hepatocyte inducible nitric oxide synthase cDNA clones, and converting the human hepatocyte inducible nitric oxide synthase cDNA clones to a plasmid vector for obtaining a substantially full length cDNA clone encoding human hepatocyte inducible nitric oxide synthase. This process further includes sequencing this cDNA, expressing the human hepatocyte inducible nitric oxide synthase cDNA protein in an expression system, and purifying the human hepatocyte inducible nitric oxide synthase cDNA protein.

It is an object of the present invention to provide for the molecular cloning and characterization of an inducible nitric oxide synthase in human tissues.

It is an object of the present invention to provide for the molecular cloning and characterization of an inducible nitric oxide synthase in human hepatocytes.

It is an object of the present invention to isolate a cDNA clone for human tissue inducible nitric oxide synthase.

It is an object of the present invention to isolate a cDNA clone for human hepatocyte inducible nitric oxide synthase.

It is an object of the present invention to provide a process for expressing and purifying human tissue inducible nitric oxide synthase enzyme.

It is an object of the present invention to provide a process for expressing and purifying human hepatocyte inducible nitric oxide synthase enzyme.

It is an object of this invention to provide for the regulation of gene expression for the human hepatocyte inducible nitric oxide synthase enzyme.

It is an object of this invention to provide for a protein including a human inducible nitric oxide synthase substantially free of other human proteins.

These and other objects of the invention will be more fully understood from the following description of the invention, the figures, the sequence listing and the claims appended hereto.

DETAILED DESCRIPTION OF THE INVENTION

As used herein, the term "patient" includes members of the animal kingdom including but not limited to human beings.

Nitric oxide is a biologic mediator derived from amino acid L-arginine. Nitric oxide synthase (NOS) acts upon L-arginine to oxidize one of the guanidino nitrogens to nitric oxide while citrulline is formed from the remainder of the L-arginine molecule. While it is understood by those skilled in the art that nitric oxide has both normal physiologic intracellular and extracellular regulatory functions, excessive production of nitric oxide is detrimental. It will be appreciated by those skilled in the art that there are no other readily available sources of human tissue inducible nitric oxide synthase. The present invention provides a cDNA clone for human tissue inducible nitric oxide synthase and a process for preparing the same. Therefore, the cloning and expression of a human tissue nitric oxide synthase cDNA of the present invention provides for a source of the enzyme for developing selective inhibitors of nitric oxide synthase.

The cloning and expression of a human tissue nitric oxide synthase cDNA of the present invention provides for a source of the enzyme in a sufficiently high concentration for providing a therapeutic purpose.

In one embodiment of this invention, a process for preparing a cDNA clone coding for a human tissue inducible nitric oxide synthase is provided. This process includes inducing the human tissue nitric oxide synthase in vitro, identifying the human tissue nitric oxide synthase messenger RNA (mRNA) by employing a cDNA probe capable of hybridizing with the human tissue inducible nitric oxide synthase mRNA, isolating the human tissue nitric oxide synthase mRNA, collecting the human tissue nitric oxide synthase mRNA, separating human tissue poly A mRNA from the human tissue nitric oxide synthase mRNA, constructing a human tissue inducible nitric oxide synthase cDNA library from the human tissue poly A mRNA using a reverse transcriptase enzyme and inserting a strand of the cDNA into a phage vector, screening the cDNA library for human tissue inducible nitric oxide synthase clones including incubating the phage vector containing the cDNA with a bacteria for forming at least one positive plaque containing the cDNA clone for human tissue inducible nitric oxide synthase, rescuing the cDNA clone from the phage vector by employing a helper phage, and converting the rescued cDNA clone to a plasmid vector for obtaining a substantially full length cDNA clone encoding human tissue inducible nitric oxide synthase.

In another embodiment of this invention, this process, as hereinbefore described, further includes excising cDNA inserts for human tissue inducible nitric oxide synthase from the plasmid vector. This process also includes confirming the cDNA inserts by employing a dideoxynucleotide DNA sequencing. Further, this process includes confirming the cDNA inserts by employing Southern blot hybridization.

In another embodiment of this Invention, the process, as hereinbefore described, includes expressing the human tissue inducible nitric oxide synthase cDNA protein in an expression system, such as for example, a bacterial expression system or a mammalian expression system.

It will be appreciated by those skilled in the art that the cloned human inducible nitric oxide synthase cDNA obtained through the methods described herein may be recombinantly expressed by molecular cloning into an expression vector containing a suitable promoter and other appropriate transcription regulatory elements, and transferred into prokaryotic or eukaryotic host cells to produce recombinant inducible nitric oxide synthase. Techniques for such manipulations are fully described in Maniatis, et al., infra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as for example bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. A variety of mammalian expression vectors may be used to express recombinant inducible nitric oxide synthase in mammalian cells.

Commercially available bacterial expression vectors which may be suitable for recombinant inducible nitric oxide synthase expression, include but are not limited to, pKC30 (ATCC 37286), pPLa2311 (ATCC 31694), pBR322 (ATCC 31344 and 37017), ptac12 (ATCC 37138), Lambda gt11 (ATCC 37194), pAS1 (ATCC 39262), pLC24, pSB226, SV40 and pKK 223-3.

Commercially available mammalian expression vectors which may be suitable for recombinant inducible nitric oxide synthase expression, include but are not limited to, pBC12B1 (ATCC 67617), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and lambda ZD35 (ATCC 37565).

DNA encoding inducible nitric oxide synthase may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL70), COS-1 (ATCC CRL1650), COS-7 (ATCC CRL1651), CHO-K1 (ATCC CCL61), 3T3 (ATCC CCL92), NIH/3T3 (ATCC CRL 1658), HeLa (ATCC CCL2), C1271 (ATCC CRL1616), BS-C-1 (ATCC CCL26) and MRC-5 (ATCC CCL171). The bacterial cell most used for expression of recombinant protein is *Escherichia coli*. There are various strains of *E. coli* available and are well known in the art.

The expression vector may be introduced into host cells via any one of a number of techniques including but not limited to transformation, transfection, protoplast fusion, and electropotation.

In a preferred embodiment of this invention, the process, as hereinbefore described, includes expressing the human tissue inducible nitric oxide synthase protein in a baculovirus expression system.

Another embodiment of this invention provides for a process, as hereinbefore described, including purifying the human tissue inducible nitric oxide synthase protein.

In a preferred embodiment of this invention, the process, as hereinbefore described, includes employing as the human tissue inducible nitric oxide synthase a human hepatocyte inducible nitric oxide synthase. This process further includes employing as the human tissue inducible nitric oxide synthase protein a human hepatocyte inducible nitric oxide synthase protein.

In another embodiment of this invention, a process is provided, as hereinbefore described, including inducing the human tissue nitric oxide synthase in vitro by stimulating a human tissue in vitro with at least one of the following (1) at least one cytokine, such as for example a cytokine selected from the group consisting of tissue necrosis factor (TNF), interleukin-1 (IL-1), and interferon-gamma (IFN-g), (2) at least one bacterial endotoxin including, such as for example, a bacterial lipopolysaccharide (LPS) and (3) combinations thereof.

A further preferred embodiment of this invention provides a process, as hereinbefore described, that includes constructing a human tissue inducible nitric oxide synthase cDNA library from the human tissue poly A mRNA using a reverse transcriptase enzyme and inserting a cDNA strand having a length of about at least 1,000 base pairs into the phage vector. In yet another preferred embodiment, a process is provided, as hereinbefore described, that includes employing lambda Zap II as the phage vector.

In another embodiment of this invention, a process is provided, as hereinbefore described, including screening the cDNA library including incubating the phage vector for about 6 to 24 hours with a bacteria at a temperature from about 34 to 40 degrees centigrade for effectuating phage lysis of the bacteria. This process further includes rescuing she cDNA clone from the phage vector by employing a helper phage such as for example ExAssist helper phage (Stratagene, La Jolla, Calif.).

In a preferred embodiment of this invention, a process, as hereinbefore described, is provided including converting the rescued cDNA clone to the plasmid vector for obtaining a substantially full length cDNA clone encoding the human tissue inducible nitric oxide synthase wherein the plasmid vector includes pBluescript (Stratagene, La Jolla, Calif.).

In another preferred embodiment of this invention, a process as hereinbefore described is provided including employing as the human tissue inducible nitric oxide synthase a human hepatocyte inducible nitric oxide synthase.

Another embodiment of this invention provides for a process for producing human hepatocyte inducible nitric oxide synthase protein comprising providing a replicatable DNA expression vector capable of expressing a DNA sequence encoding human hepatocyte inducible nitric oxide synthase in a suitable host, transforming the host for obtaining a recombinant host, and maintaining the recombinant host under conditions permitting expression of the DNA sequence to provide human hepatocyte inducible nitric oxide synthase.

Another embodiment of this invention provides a human tissue inducible nitric oxide synthase cDNA clone. A preferred embodiment of this invention provides a human hepatocyte inducible nitric oxide synthase cDNA clone. The human hepatocyte inducible nitric oxide synthase cDNA clone of this invention has a cDNA coding for the amino acid sequence, SEQ ID NOS: 1 and 2 shown in FIGS. 1A–G. FIGS. 1A–G show the cDNA sense sequence (top line of each horizontal row) and the deduced amino acid sequence of amino acids 1– 1153 (bottom line of each horizontal row) for the cDNA clone for the human hepatocyte inducible nitric oxide synthase of this invention. FIGS. 1A–G show that the cDNA sequence for the human hepatocyte inducible nitric oxide synthase of this invention is 4,145 nucleotide bases long with the start codon beginning at base number 207 and the stop codon ending at base number 3668. The cDNA double strand sequence was determined using the Sanger dideoxynucleotide sequence technique well known by those skilled in the art on a Genesis 2000 sequencing system (USB, Cleveland, Ohio). *Proc. Natl. Acad. Sci. USA*, Vol 74, p. 5463 (1977).

Another embodiment of this invention provides a human tissue inducible nitric oxide synthase recombinant protein expressed from a human tissue inducible nitric oxide synthase cDNA clone. In a preferred embodiment, a human hepatocyte inducible nitric oxide synthase recombinant protein expressed from a human hepatocyte inducible nitric oxide synthase cDNA clone is provided.

Another embodiment of this invention provides for a protein comprising a human inducible nitric oxide synthase substantially free of other human proteins.

Another embodiment of this invention provides for an isolated DNA sequence encoding human inducible nitric oxide synthase consisting essentially of an initiation codon positioned upstream and adjacent to an open reading frame consisting essentially of a DNA sequence encoding human inducible nitric oxide synthase.

A further embodiment of this invention provides for an isolated DNA sequence encoding human inducible nitric oxide synthase consisting essentially of an initiation codon positioned upstream and adjacent to an open reading frame consisting essentially of a DNA sequence encoding human inducible nitric oxide synthase protein. The human inducible nitric oxide synthase protein begins at the initiation codon and terminates at a stop codon.

In yet another embodiment of this invention a recombinant plasmid is provided containing a recombinant plasmid pHINOS having a deposit accession number ATCC 75358 deposited with the American Type Culture Collection. A further embodiment of this invention provides for bacteria transformed by the recombinant plasmid pHINOS.

In another embodiment of this invention a microorganism is provided containing a HINOS cDNA plasmid transformed in *E. coli* SOLR bacteria having a deposit accession number ATCC 69126 deposited with the American Type Culture Collection.

EXAMPLE 1

INDUCING HUMAN HEPATOCYTE INDUCIBLE NITRIC OXIDE SYNTHASE mRNA is weakly induced following stimulation with cytokine signals such as for example tumor necrosis factor (TNF), interleukin-1 (IL-1) or interleukin-gamma (IFN-g). Cytokine signals synergize to further up-regulate mRNA levels and nitric oxide synthase activity. Maximum induction was achieved with a combination of TNF, IL-1, IFN-g and bacterial lipopolysaccharide (LPS). *FASEB, Journal*, Vol. 6, supra, and *J. Exp. Med.*, Vol. 176, supra.

EXAMPLE 2

IDENTIFYING AND ISOLATING HUMAN HEPATOCYTE NITRIC OXIDE SYNTHASE mRNA

A cDNA probe capable of hybridizing with human hepatocyte inducible nitric oxide synthase mRNA was used for identifying and isolating the mRNA for human hepatocyte inducible nitric oxide synthase. The time-point of peak mRNA levels following cytokine and LPS [hereinafter cytokine mixture (CM)] stimulation was then determined.

Total RNA was extracted about 2–48 hours following CM-stimulation of cultured human hepatocytes using the RNAzol B modified method of Chomczynski and Sacchi. *Anal Biochem.*, Vol 162; pp. 156–159 (1987). Northern blot analysis was performed on 20 microgram (ug) aliquots of total RNA using a murine macrophage cDNA probe, representing an excision fragment produced by Not I restriction enzyme [*Proc. Natl. Acad. Sci. USA.*, Vol 89, pp. 6711–6715 (1992) GenBank Accession No. M92649] and cross-species hybridization. The human hepatocyte nitric oxide synthase mRNA was identified as a single band at about 4.5 kb (kilobase) with maximal mRNA levels seen about 8 hours after stimulation.

Figure 3:
FIG. 3 shows a Northern Blot of induced nitric oxide synthase mRNA isolated from three separate human liver samples using mouse macrophage cDNA.

FIG. 2 shows the presence of the 4.5 kb message for human hepatocyte inducible nitric oxide synthase. Human hepatocytes (HC) that were freshly isolated were placed in cell culture and exposed to a combination of human recombinant tumor necrosis factor (500 units/milliliter), human recombinant interleukin-1 (5 units/milliliter), human recombinant interferon-gamma (100 units/milliliter), and lipopolysaccharide (10 micrograms/milliliter). FIG. 2 shows that at the indicated time points (2 hours, 4 hours, 6 hours and 8 hours) total RNA was isolated and that 20 micrograms per sample was subjected to Northern Blot analysis. A 2.7 Kb fragment of cDNA to murine macrophage inducible nitric oxide synthase was used to hybridize with the mRNA for human hepatocyte inducible nitric oxide synthase. FIG. 2 demonstrates that the 4.5 Kb message peaked at about 8 hours following stimulation. FIG. 2 shows that no mRNA signal was detected in control (unstimulated) hepatocytes. FIG. 3 shows the expression of the 4.5 Kb mRNA for human hepatocyte inducible nitric oxide synthase at about 8 hours after exposure to the above mentioned signals for hepatocytes isolated from three separate individuals [patient (Pt.) 1, 2, and 3]. FIG. 3 demonstrates that no signal was detected in control (unstimulated) hepatocytes.

Figure 4:
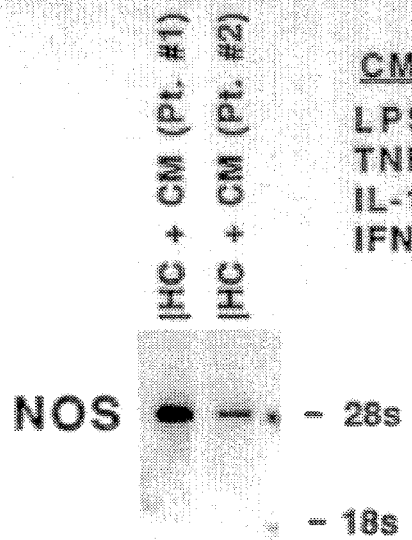
FIG. 4 shows a Northern Blot of poly A mRNA purified from 2 separate human liver samples for the construction of the cDNA library for isolation of the cDNA clone for the human hepatocyte inducible nitric oxide synthase.

Because the 8 hour time point yielded maximal mRNA levels, samples of RNA were isolated from two human livers about 8 hours following CM-stimulation in vitro and were pooled to obtain sufficient quantity for the cDNA library construction. The cDNA synthesis requires about from 10 to 20 micrograms of poly A mRNA rather than total RNA. To obtain purified poly A mRNA, poly A mRNA was separated from total RNA by elution through an oligo-dT cellulose column. The purity of the mRNA was assessed by repeat Northern blot analysis which included subjecting 0.5 micrograms of poly A RNA from each of the two human livers to Northern Blot analysis using the 2.7 Kb cDNA from murine macrophage inducible nitric oxide synthase. FIG. 4 shows strong nitric oxide synthase mRNA bands from 2 different patients without evidence of degraded poly A RNA.

FIG. 4 shows that the murine macrophage inducible nitric oxide synthase cross hybridizes with the human hepatocyte inducible nitric oxide synthase poly A RNA and effectively identifies the mRNA for human hepatocyte inducible nitric oxide synthase. These samples of poly A RNA were used to construct the cDNA library for isolation of the cDNA clone for the human hepatocyte inducible nitric oxide synthase.

EXAMPLE 3

CONSTRUCTING A HUMAN HEPATOCYTE INDUCIBLE NITRIC OXIDE SYNTHASE cDNA LIBRARY

Using about 20 micrograms of poly A RNA enriched for hepatocyte nitric oxide synthase mRNA by CM-stimulation, a cDNA library was constructed by Stratagene, La Jolla, Calif. The first strand cDNA was synthesized from the human hepatocyte poly A RNA using reverse transcriptase enzyme with random and oligo-dT primers. After size exclusion for a minimum of about 1000 nucleotide base pair length, the cDNA's were inserted into a lambda Zap II phage vector (Stratagene, La Jolla, Calif.) and was titered.

EXAMPLE 4

SCREENING THE cDNA LIBRARY FOR HUMAN HEPATOCYTE INDUCIBLE NITRIC OXIDE SYNTHASE cDNA CLONES

Figure 5:
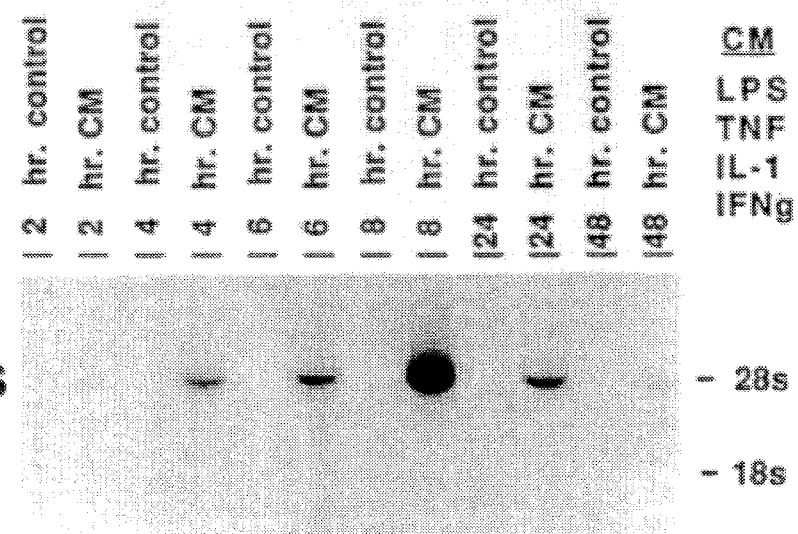
FIG. 5 shows a Northern Blot using cDNA isolated from human hepatocytes that sets forth the time course of induction of human nitric oxide synthase mRNA following cytokine and LPS stimulation.

To screen the cDNA library, $1 \times 10^6$ phage were incubated with bacteria (*E. coli* Sure strain) at about 34 to 40 degrees centigrade for about 15 to 30 minutes. This mixture was added to molten agarose and poured onto 20×20 centimeter agar plates at a density of about $2 \times 10^5$ plaques/plate (Maniatis et al., *Molecular Cloning: A Laboratory Manual*, Cold Spring Harbor Laboratory, Cold Spring Harbor, N.Y., 1982). The plates were incubated from about 34 to 40 degrees centigrade overnight from about 6 to 24 hours to allow for phage lysis of bacteria. The plaques were then transferred to nylon filters and positive clones were identified by filter hybridization with $^{32}$P-labeled murine macrophage nitric oxide synthase cDNA probe. Positive clones were cored from the agar plates after localization by autoradiograph alignment. This procedure was repeated about 3 times until individual clones were isolated. The positive clones were rescued from the lambda Zap II phage vector using a helper phage ExAssist (Stratagene, La Jolla, Calif.), and then converted to the plasmid vector, pBluescript (Stratagene, La Jolla, Calif.). The cDNA inserts for human hepatocyte inducible nitric oxide synthase were excised from the Bluescript plasmid cloning sites by restriction analysis with EcoRI enzyme and then sized by gel electrophoresis. The cDNA insert identities were confirmed by DNA sequencing and by Southern blot hybridization with the murine macrophage cDNA clone. In addition, repeat Northern blot analysis was performed on cytokine-stimulated human hepatocytes in culture using the human nitric oxide synthase cDNA clone of this invention as probe. FIG. 5 shows a time course for mRNA expression for human hepatocyte inducible nitric oxide synthase. This RNA is from an individual patient different from the patients listed in FIGS. 2 and 3. The cells of the patient in FIG. 5 were exposed to the same agents as described for FIG. 2. FIG. 5 shows the human nitric oxide synthase cDNA identifying the same mRNA signal as the macrophage probe, thus, further confirming its identify. It is important to note that the isolated cDNA clone coding for human inducible nitric oxide synthase of this invention was used to hybridize with the mRNA, thus, confirming the capacity of the cDNA clone of this invention to identify the human hepatocyte inducible nitric oxide synthase mRNA.

EXAMPLE 5 cDNA SEQUENCING

The plasmid vector pBluescript contains universal primer regions which were used to facilitate double-stranded DNA sequencing. Positive clones were sequenced by using the dideoxynucleotide technique of Sanger, supra, with the Genesis 2000 sequencing system (USB, Cleveland, Ohio). Sequence analysis was done using Genbank DNA sequencing software programs available through the Pittsburgh Supercomputing Center (Billiar TR., Pittsburgh Supercomputing Center, Pittsburgh, Pa.).

EXAMPLE 6

EXPRESSING HUMAN HEPATOCYTE INDUCIBLE NITRIC OXIDE SYNTHASE

Verification of the full length cDNA identify was accomplished by expressing the recombinant human hepatocyte inducible nitric oxide synthase protein. The human hepatocyte inducible nitric oxide synthase clone was ligated into the pCIS expression vector (Genentech, Calif.) which utilizes a CMV promoter. Next the expression vector was transfected into human embryonic kidney 293 cells (ATCC, Maryland). Nitric oxide synthase activity was assessed by measuring the conversion of [$^3$H] arginine to [$^3$H] citrulline. It will be appreciated by those skilled in the art that this expression system was successfully used for expression of the cloned rat brain constitutive nitric oxide synthase, and there was negligible nitric oxide synthase activity in the unstimulated 293 kidney cells [Bredt et al., *Nature*, Vol 351, p. 714 (1991)]. After the identity of the human hepatocyte inducible nitric oxide synthase clone of this invention was verified as hereinbefore described, the cDNA was expressed in a baculovirus expression system (Invitrogen, San Diego, Calif.) which allowed for large scale enzyme production. *Texas Agriculture Experiment Station Bulletin*, No. 1555 (1988). More specifically, the human hepatocyte nitric oxide synthase cDNA was inserted into the baculovirus transfer vector and then co-transfected with wild type viral DNA into Sf9 insect cells (ATCC, Maryland). Recombinant viral plaques were isolated to allow for protein over-expression.

EXAMPLE 7

PURIFYING THE HUMAN HEPATOCYTE INDUCIBLE NITRIC OXIDE SYNTHASE PROTEIN

The resultant human hepatocyte inducible nitric synthase protein was purified using a two step procedure. First, the protein was passed through an anion-exchange column of DEAE cellulose. This was followed by affinity chromatography with 2', 5'-ADP Sepharose [Evans et al , *Proc. Natl. Acad. Sci. USA*, Vol 89, pp 5361–5365 (1992)] Purity was assessed by SDS-polyacrylamide gel electrophoresis. Activity was quantitated after each step by measuring the ability of the enzyme to generate $NO_2^-$ and $NO_3^-$ from L-arginine. $NO_2^-$ and $NO_3^-$ was measured using an automated colorimetric reaction based on the Greiss reaction [Green et al., *Anal. Biochem.*, Vol. 126, p. 131 (1982)].

Whereas, particular embodiments of this invention have been described above for purposes of illustration, it will be evident to those persons skilled in the art that numerous variations of the details of the present invention may be made without departing from the invention as defined in the appended claims that follow the SEQUENCE LISTING.

What is claimed:

1. An isolated nucleic acid molecule comprising a nucleotide sequence encoding a human inducible nitric oxide synthase protein.

2. A DNA vector molecule comprising said nucleotide sequence of claim 1.

3. A host cell transformed with said DNA vector molecule of claim 2.

4. A host cell of claim 3 which is a bacterial host cell.

5. An isolated nucleic acid molecule comprising a nucleotide sequence expressing a human inducible protein which is SEQ ID NO:2, extending from the initiating methionine numbered amino acid residue 1 through amino acid residue number 1153.

6. A DNA vector molecule comprising said nucleotide sequence of claim 5.

7. A eukaryotic host cell transformed with said DNA vector molecule of claim 6.

8. A prokaryotic host cell transformed with said DNA vector molecule of claim 6.

9. An isolated nucleic acid molecule comprising the DNA sequence as set forth in SEQ ID NO: 1, a portion thereof extending from nucleotide 207 through nucleotide position 3665, inclusive, which encodes a human inducible nitric oxide synthase protein.

10. A DNA vector molecule comprising said nucleotide sequence of claim 9.

11. A host cell transformed with said DNA vector molecule of claim 10.

12. A host cell of claim 11 which is a bacterial host cell.

13. The isolated DNA molecule designated by SEQ ID NO:1, a portion thereof extending from nucleotide 207 through nucleotide position 3665, inclusive, which encodes the human inducible nitric oxide synthase protein.

14. A DNA vector molecule comprising said nucleotide sequence of claim 13.

15. A host cell transformed with said DNA vector molecule of claim 14.

16. A host cell of claim 15 which is a bacterial host cell.

17. The DNA vector molecule of claim 14 which is pHINOS, having the accession number ATCC 75358.

18. A bacterial host cell transformed with said pHINOS DNA vector molecule of claim 17.

19. The transformed bacterial host of claim 18 which is *E. coli* SOLR, having the accession number ATCC 69126.

20. The portion of said isolated DNA molecule of claim 13 encoding the human inducible nitric oxide synthase protein.

21. A DNA vector molecule comprising said nucleotide sequence of claim 20.

22. A host cell transformed with said DNA vector molecule of claim 21.

23. A host cell of claim 22 which is a bacterial host cell.

* * * * *